US010415086B2

(12) United States Patent
Kornilovich et al.

(10) Patent No.: US 10,415,086 B2
(45) Date of Patent: *Sep. 17, 2019

(54) POLYMERASE CHAIN REACTION SYSTEMS

(71) Applicant: Hewlett-Packard Development Company, L.P., Houston, TX (US)

(72) Inventors: Pavel Kornilovich, Corvallis, OR (US); Erik D. Tornianinen, Maple Grove, OR (US); Alexander Govyadinov, Corvallis, OR (US); David P. Markel, Albany, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/955,364

(22) Filed: Apr. 17, 2018

(65) Prior Publication Data

US 2018/0230518 A1 Aug. 16, 2018

Related U.S. Application Data

(63) Continuation of application No. 13/069,630, filed on Mar. 23, 2011, now Pat. No. 9,963,739, which is a
(Continued)

(51) Int. Cl.
*C12Q 1/686* (2018.01)
*B01L 3/00* (2006.01)
*B01L 7/00* (2006.01)

(52) U.S. Cl.
CPC .......... *C12Q 1/686* (2013.01); *B01L 3/50273* (2013.01); *B01L 7/525* (2013.01);
(Continued)

(58) Field of Classification Search
CPC ................. B01L 3/50273; B01L 7/525; B01L 2300/1827; B01L 2300/0681; B01L 2300/0867; B01L 2200/10
See application file for complete search history.

(56) References Cited

U.S. PATENT DOCUMENTS 3,552,207 A 1/1971 Monk et al.
3,856,467 A 12/1974 Picker
(Continued)

FOREIGN PATENT DOCUMENTS

CA 2444525 4/2004
CN 1498761 5/2004
(Continued)

OTHER PUBLICATIONS

Nguyen et al., "A Stepper Micropump for Ferrofluid Driven Microfluidic Systems"; http://www.bentham.org/mns/samples/mns%201-1/0004MNS.pdf> Publication Date: 2009; pp. 17-21.
(Continued)

*Primary Examiner* — William H. Beisner
*Assistant Examiner* — Danielle B Henkel
(74) *Attorney, Agent, or Firm* — Michael A Dryja

(57) ABSTRACT

In one embodiment, a polymerase chain reaction (PCR) system includes a mixture chamber, a denature chamber, an annealing chamber, an extension chamber, and a product chamber, that are fluidically coupled to one another through a plurality of microfluidic channels. An inertial pump is associated with each microfluidic channel, and each inertial pump includes a fluid actuator integrated asymmetrically within its associated microfluidic channel. The fluid actuators are capable of selective activation to circulate fluid between the chambers in a controlled cycle.

19 Claims, 15 Drawing Sheets

Related U.S. Application Data continuation-in-part of application No. PCT/US2011/024830, filed on Feb. 15, 2011, which is a continuation-in-part of application No. PCT/US2011/023173, filed on Jan. 31, 2011, which is a continuation-in-part of application No. PCT/US2011/021168, filed on Jan. 31, 2011, which is a continuation-in-part of application No. PCT/US2010/054412, filed on Oct. 28, 2010, which is a continuation-in-part of application No. PCT/US2010/054458, filed on Oct. 28, 2010, which is a continuation-in-part of application No. PCT/US2010/043480, filed on Jul. 28, 2010, which is a continuation-in-part of application No. 12/833,984, filed on Jul. 11, 2010, now Pat. No. 8,540,355, which is a continuation-in-part of application No. PCT/US2010/035697, filed on May 21, 2010.

(52) U.S. Cl.
CPC ... *B01L 2200/10* (2013.01); *B01L 2300/0681* (2013.01); *B01L 2300/0867* (2013.01); *B01L 2300/1827* (2013.01)

(56) References Cited

U.S. PATENT DOCUMENTS

| | | |
|---|---|---|
| 4,318,114 A | 3/1982 | Huliba |
| 5,412,411 A | 5/1995 | Anderson |
| 5,807,749 A | 9/1998 | Hornemann |
| 5,818,485 A | 10/1998 | Rezanka |
| 5,820,260 A | 10/1998 | Vander Heyden et al. |
| 6,010,316 A | 1/2000 | Haller et al. |
| 6,017,117 A | 1/2000 | McClelland |
| 6,055,002 A | 4/2000 | Wen et al. |
| 6,079,873 A | 6/2000 | Cavicchi et al. |
| 6,106,091 A | 8/2000 | Osawa et al. |
| 6,152,559 A | 11/2000 | Kojima |
| 6,193,413 B1 | 2/2001 | Lieberman |
| 6,227,660 B1 | 5/2001 | McClelland et al. |
| 6,227,824 B1 | 5/2001 | Stehr |
| 6,244,694 B1 | 6/2001 | Weber |
| 6,283,718 B1 | 9/2001 | Prosperetti et al. |
| 6,351,879 B1 | 3/2002 | Furlani et al. |
| 6,360,775 B1 | 3/2002 | Barth et al. |
| 6,431,694 B1 | 8/2002 | Ross |
| 6,450,773 B1 | 9/2002 | Upton |
| 6,467,887 B2 | 10/2002 | Lopez et al. |
| 6,481,984 B1 | 11/2002 | Shinohara |
| 6,568,799 B1 | 5/2003 | Yang et al. |
| 6,631,983 B2 | 10/2003 | Romano, Jr. et al. |
| 6,655,924 B2 | 12/2003 | Ma |
| 6,730,206 B2 | 5/2004 | Ricco et al. |
| 6,752,493 B2 | 6/2004 | Dowell et al. |
| 6,910,797 B2 | 6/2005 | Falcon |
| 6,953,236 B2 | 10/2005 | Silverbrook |
| 7,025,323 B2 | 4/2006 | Krulevitch et al. |
| 7,040,745 B2 | 5/2006 | Kent |
| 7,049,558 B2 | 5/2006 | Baer et al. |
| 7,094,040 B2 | 8/2006 | Higashino |
| 7,097,287 B2 | 8/2006 | Nakao et al. |
| 7,118,189 B2 | 10/2006 | Kuester et al. |
| 7,182,442 B2 | 2/2007 | Sheinman |
| 7,204,585 B2 | 4/2007 | Bruinsma et al. |
| 7,217,395 B2 | 5/2007 | Sander |
| 7,291,512 B2 | 11/2007 | Unger |
| 7,427,274 B2 | 9/2008 | Harris et al. |
| 7,470,004 B2 | 12/2008 | Eguchi et al. |
| 7,543,923 B2 | 6/2009 | McNestry |
| 7,647,860 B2 | 1/2010 | Creswell |
| 7,727,478 B2 | 6/2010 | Higashino |
| 7,762,719 B2 | 7/2010 | Fon et al. |
| 7,763,453 B2 | 7/2010 | Clemmens et al. |
| 7,784,495 B2 | 8/2010 | Prakash et al. |
| 7,832,429 B2 | 11/2010 | Young et al. |
| 7,871,160 B2 | 1/2011 | Kang et al. |
| 8,286,656 B2 | 10/2012 | Rastegar |
| 8,329,118 B2 | 12/2012 | Padmanabhan et al. |
| 8,439,481 B2 | 5/2013 | Xie et al. |
| 8,540,355 B2 * | 9/2013 | Govyadinov .......... B41J 2/1404 347/54 |
| 8,651,646 B2 | 2/2014 | Govyadinov et al. |
| 8,757,783 B2 | 6/2014 | Govyadinov et al. |
| 8,939,531 B2 | 1/2015 | Govyadinov et al. |
| 9,090,084 B2 | 7/2015 | Govyadinov |
| 9,963,739 B2 * | 5/2018 | Kornilovich .......... C12Q 1/686 |
| 2001/0030130 A1 | 10/2001 | Ricco et al. |
| 2002/0009374 A1 | 1/2002 | Higashino |
| 2002/0079008 A1 | 6/2002 | Chien et al. |
| 2002/0098122 A1 | 7/2002 | Singh et al. |
| 2002/0156383 A1 | 10/2002 | Altman |
| 2002/0197167 A1 | 12/2002 | Kornelsen |
| 2003/0086790 A1 | 5/2003 | Ma |
| 2003/0215342 A1 | 11/2003 | Higashino |
| 2004/0024002 A1 | 2/2004 | Burnett et al. |
| 2004/0063217 A1 | 4/2004 | Webster |
| 2004/0180377 A1 | 9/2004 | Manger et al. |
| 2004/0200724 A1 | 10/2004 | Fujii et al. |
| 2004/0202548 A1 | 10/2004 | Dai et al. |
| 2005/0052513 A1 | 3/2005 | Inoue |
| 2005/0069425 A1 | 3/2005 | Gray et al. |
| 2005/0092662 A1 | 5/2005 | Gilbert et al. |
| 2005/0129529 A1 | 6/2005 | Cho |
| 2005/0196304 A1 | 9/2005 | Richter et al. |
| 2005/0220630 A1 | 10/2005 | Bohm |
| 2005/0249607 A1 | 11/2005 | Klee |
| 2005/0282054 A1 | 12/2005 | Ishida et al. |
| 2006/0046300 A1 | 3/2006 | Padmanabhan et al. |
| 2006/0051218 A1 | 3/2006 | Harttig |
| 2006/0123892 A1 | 6/2006 | Brekelmans et al. |
| 2007/0026421 A1 | 2/2007 | Sundberg et al. |
| 2007/0286254 A1 | 12/2007 | Fon et al. |
| 2007/0291082 A1 | 12/2007 | Baumer et al. |
| 2008/0007604 A1 | 1/2008 | Kang et al. |
| 2008/0047836 A1 | 2/2008 | Strand et al. |
| 2008/0050283 A1 | 2/2008 | Chou et al. |
| 2008/0055378 A1 | 3/2008 | Drury et al. |
| 2008/0079791 A1 | 4/2008 | Kang et al. |
| 2008/0087584 A1 | 4/2008 | Johnson et al. |
| 2008/0118790 A1 | 5/2008 | Kim et al. |
| 2008/0138247 A1 | 6/2008 | Inganas et al. |
| 2008/0143793 A1 | 6/2008 | Okuda |
| 2008/0260582 A1 | 10/2008 | Gauer et al. |
| 2009/0007969 A1 | 1/2009 | Gundel |
| 2009/0014360 A1 | 1/2009 | Toner et al. |
| 2009/0027429 A1 | 1/2009 | Jung |
| 2009/0027458 A1 | 1/2009 | Leighton et al. |
| 2009/0038938 A1 | 2/2009 | Mezic et al. |
| 2009/0040257 A1 | 2/2009 | bergstedt et al. |
| 2009/0052494 A1 | 2/2009 | Wijffels |
| 2009/0079789 A1 | 3/2009 | Silverbrook |
| 2009/0128922 A1 | 5/2009 | Justis et al. |
| 2009/0147822 A1 | 6/2009 | Tokhtuev et al. |
| 2009/0148933 A1 | 6/2009 | Battrell et al. |
| 2009/0246086 A1 | 10/2009 | Barbier et al. |
| 2009/0270834 A1 | 10/2009 | Nisato et al. |
| 2009/0297372 A1 | 12/2009 | Amirouche et al. |
| 2010/0013887 A1 | 1/2010 | Suh |
| 2010/0024572 A1 | 2/2010 | Roukes et al. |
| 2010/0101764 A1 | 4/2010 | Yang |
| 2010/0173393 A1 | 7/2010 | Handique et al. |
| 2010/0212762 A1 | 8/2010 | Toonder et al. |
| 2010/0328403 A1 | 12/2010 | Xie |
| 2011/0240752 A1 | 10/2011 | Meacham |
| 2011/0286493 A1 | 11/2011 | Torniainen et al. |
| 2012/0015376 A1 | 1/2012 | Bornhop |
| 2012/0098907 A1 | 4/2012 | Xie et al. |
| 2012/0244604 A1 | 9/2012 | Kornilovich et al. |
| 2013/0061936 A1 | 3/2013 | Govyadinov et al. |
| 2013/0061962 A1 | 3/2013 | Kornilovich |

(56) References Cited

U.S. PATENT DOCUMENTS

| | | |
|---|---|---|
| 2013/0083136 A1 | 4/2013 | Govyadinov et al. |
| 2015/0091989 A1 | 4/2015 | Govyadinov |
| 2015/0273853 A1 | 10/2015 | Govyadinov et al. |

FOREIGN PATENT DOCUMENTS

| | | |
|---|---|---|
| CN | 1678460 | 10/2005 |
| CN | 101100137 | 1/2008 |
| CN | 101267885 | 9/2008 |
| CN | 101287606 | 10/2008 |
| CN | 101306792 | 11/2008 |
| CN | 1673528 | 2/2009 |
| CN | 101391530 | 3/2009 |
| CN | 102971150 A1 | 3/2013 |
| CN | 102985261 A | 3/2013 |
| CN | 103003577 | 3/2013 |
| CN | 103153627 A | 6/2013 |
| CN | 103025530 | 6/2015 |
| CN | 102985831 | 1/2016 |
| EP | 0568902 | 4/1993 |
| EP | 1052099 | 11/2000 |
| EP | 1518683 | 3/2005 |
| EP | 2018969 | 1/2009 |
| JP | 0526170 | 2/1993 |
| JP | 10175307 | 6/1998 |
| JP | 2001205810 | 7/2001 |
| JP | 2001-322099 | 11/2001 |
| JP | 2003-527616 | 9/2003 |
| JP | 2003528276 | 9/2003 |
| JP | 2003-286940 | 10/2003 |
| JP | 2003286940 | 10/2003 |
| JP | 2003-534538 | 11/2003 |
| JP | 2004-513342 | 4/2004 |
| JP | 2004-169706 | 6/2004 |
| JP | 2004-190614 | 7/2004 |
| JP | 2004249741 | 9/2004 |
| JP | 2005125668 | 5/2005 |
| JP | 2006510854 | 3/2006 |
| JP | 2006512545 | 4/2006 |
| JP | 2006156894 | 6/2006 |
| JP | 2006272614 | 10/2006 |
| JP | 2007224844 | 9/2007 |
| JP | 2008162270 | 7/2008 |
| JP | 2009117344 | 5/2009 |
| JP | 2009190370 | 8/2009 |
| JP | 2013529566 | 7/2013 |
| JP | 5631501 | 11/2014 |
| JP | 5746342 | 7/2015 |
| JP | 5756852 | 7/2015 |
| JP | 2015211965 | 11/2015 |
| KR | 20030059797 | 7/2003 |
| KR | 20080004095 | 1/2008 |
| KR | 20090082563 | 7/2009 |
| KR | 20090108371 | 10/2009 |
| KR | 20130050344 | 5/2013 |
| KR | 20130113957 | 10/2013 |
| KR | 20130118222 | 10/2013 |
| KR | 20130137638 | 12/2013 |
| TW | I458645 | 11/2014 |
| WO | WO-0171226 | 9/2001 |
| WO | WO-2008091294 | 7/2008 |
| WO | WO-2011146069 | 11/2011 |
| WO | WO-2011146145 | 11/2011 |
| WO | WO-2011146156 | 11/2011 |
| WO | WO-2012008978 | 1/2012 |
| WO | WO-2012015397 | 2/2012 |
| WO | WO-2012057758 | 5/2012 |

OTHER PUBLICATIONS

Hany et al; Thermal Analysis of Chemical Reaction With a Continuous Microfluidic Calorimeter; Chemical Engineering Journal 160 (2010); Jul. 10, 2009; pp. 814-822.

Leslie et. al.; "Frequency-specific Flow Control in Microfluidic Circuits with Passive Elastomeric Features; Nature Physics"; Feb. 1, 2009; pp. 231-235.

Fadl et al; "The effect of the Microfluidic Diodicity on the Efficiency of Valve-Less Rectification Micropumps Using Lattice Boltzmann Method"; Microsyst Technol; Jul. 2009.

Inkjet Photo Printers, Ink, Paper, and Laser Toner Too!; InkJet Printers Paper Reviews; inkjethelper.com, retrieved Oct. 26, 2010, 20 pp.

Koltay et al; "Non-Contact Liquid Handling: Basics and Technologies"; http://www.labautopedia.com/mw/index.php/Non-Contact Liquid Handling: Basics and Technologies, 2010.

Yeo et al, Fast Inertial Microfluidic Actuation and Manipulation Using Surface Acoustic Waves; FEDSM-ICNMM2010 Meeting; Aug. 1-5, 2010, pp. 1-8.

Zhang et al. "Micropumps, Microvalves, and Micromixers Within Pcr Microfluidic Chips: Advances and Trends"; Biotech Adv. 2007, 483-514.

Ramirez-Garciaa, et.al.; Towards the Development of a Fully Integrated Polymeric Microfluidic Platform for Environmental Analysis; Elesvier B.V.; Apr. 12, 2008; pp. 46.

* cited by examiner

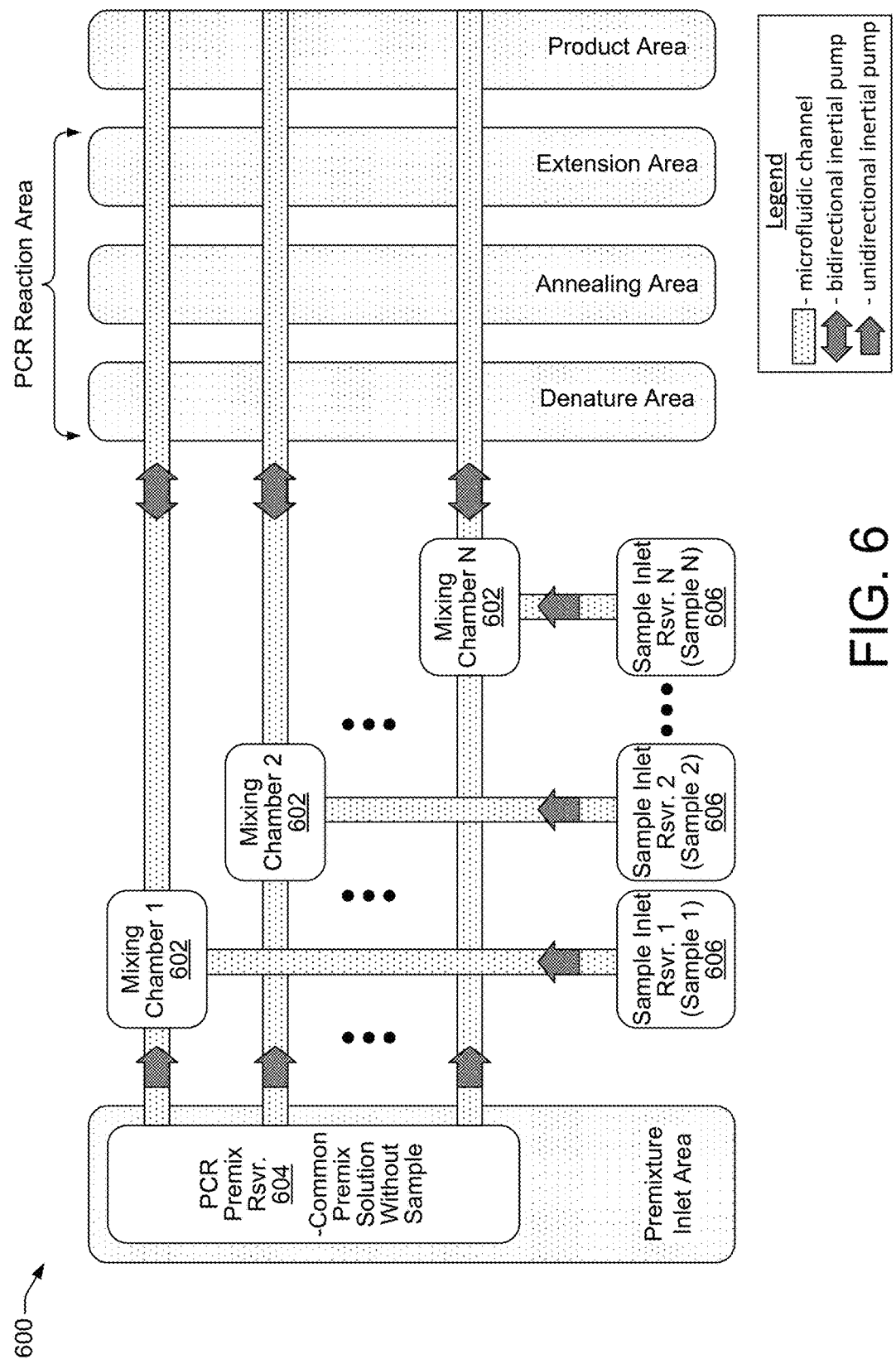

POLYMERASE CHAIN REACTION SYSTEMS

RELATED APPLICATIONS

This application claims priority from, and incorporates in their entirety, the following patent applications: Application No. PCT/US2010/035697, filed May 21, 2010; Application Ser. No. 12/833,984, filed Jul. 11, 2010 and issued as U.S. Pat. No. 8,540,355; Application No. PCT/US2010/043480, filed Jul. 28, 2010; Application No. PCT/US2010/054412, filed Oct. 28, 2010; Application No. PCT/US/054458, filed Oct. 28, 2010; Application No. PCT/US2011/021168, filed Jan. 13, 2011; Application No. PCT/US2011/023173, filed Jan. 31, 2011; Application No. PCT/2011/024830, filed Feb. 15, 2011; Application Ser. No. 13/069,630, filed Mar. 23, 2011 and issued as U.S. Pat. No. 9,963,739.

BACKGROUND

The polymerase chain reaction (PCR) is a process where a single DNA molecule can be amplified (replicated) by orders of magnitude into thousands or millions of copies of the molecule. The process relies on cycling a PCR mixture containing polymerase, dNTPs (deoxyribonucleotides), sample DNA template, and primers through different temperatures. At a first, high-temperature range, denaturation occurs as the paired strands of the double-stranded sample DNA template separate into two individual strands. At a second, low-temperature range, annealing of primers complementary to the region of the sample DNA template being targeted for amplification takes place. At a third, mid-temperature range, extension of the complementary sequence from the primer occurs, during which the polymerase adheres to the primer and uses nucleotides to replicate each isolated sample DNA template strand. This cycle is typically repeated (e.g., from 20-40 times) to increase the amount of replicated DNA on an exponential basis until the desired amount is present for a particular experiment. In general, the PCR amplification process has become an indispensable part of genetic analysis in various areas including molecular biology, diagnostics, forensics, agriculture, and so on.

Efforts to reduce the time and costs associated with the PCR process are ongoing. One area of development is in microfluidic devices which provide a miniaturized environment for the PCR process that enables a reduction in both the volume of PCR mixture and the time needed for PCR temperature cycling. Small devices such as microfluidic chips have a reduced thermal mass that enables the mixtures to be cycled through different temperatures in the denaturing, annealing and extending steps at increased speeds, which reduces the overall time needed for completing the PCR process. In addition, increased integration in PCR systems that include such microfluidic chips has resulted in the use of microfluidic mixers, valves, pumps, channels, chambers, heaters and sensors. However, the pumping and mixing components in such systems are typically not integrated into the microfluidic chips themselves. Instead, these components are generally external to the microfluidic chip, which increases the size of the integrated system and raises the costs of fabrication.

BRIEF DESCRIPTION OF THE DRAWINGS

The present embodiments will now be described, by way of example, with reference to the accompanying drawings, in which:

FIG. 6 shows a parallel, linear-type, inertial pump-based, PCR architecture that includes dedicated mixing chambers and is suitable for implementation on a PCR microchip, according to an embodiment;

DETAILED DESCRIPTION

Overview of Problem and Solution

Figure 1:
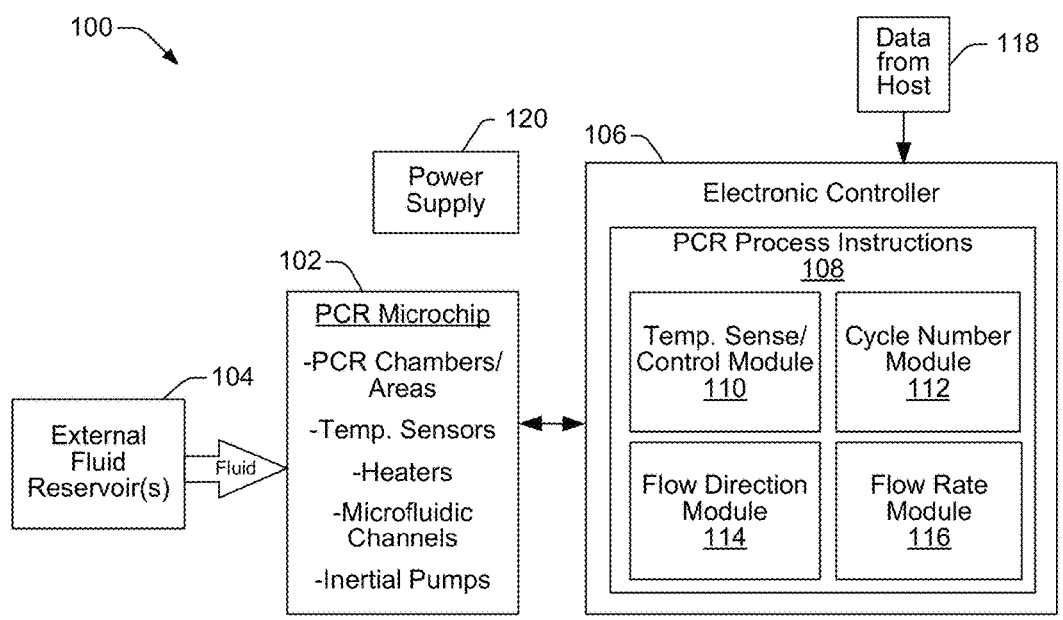
FIG. 1 shows a polymerase chain reaction (PCR) system, according to an embodiment.

As noted above, microfluidic chips are being developed to help reduce the time and costs associated with polymerase chain reaction (PCR). The two basic types of PCR microfluidic chips are a stationary-chamber type chip, and a flow-through type chip. In a stationary-chamber chip, the PCR mixture (including the sample DNA template) is placed in a reaction chamber and temperature cycled without moving the mixture around. One problem with implementing the PCR process in this manner is that the PCR mixture is not the only thing being temperature cycled. Instead, a larger thermal mass that includes the entire mixture, the reaction chamber, and the surrounding environment (i.e., the entire chip) must all be repeatedly heated and cooled. Disadvantages associated with heating and cooling this large thermal mass include the additional time and external power needed to complete the temperature cycling.

In a flow-through chip, the PCR mixture is moved through a channel that repeatedly passes through the three PCR temperature zones (i.e., in the denature, annealing, and extension steps). Since the temperature zones can be heated once and then maintained, only the mixture itself (or even just a portion of the mixture) is temperature cycled. The mixture reaches the appropriate temperature in each step of the cycle much faster and with much less energy being expended.

However, one disadvantage with the flow-through chip configuration is that it requires a pump to move the fluidic mixture. Traditional pumps used in conjunction with flow-through chips have included external syringes, pneumatic, peristaltic, rotary, electrophoretic, electromagnetic, electrowetting, and capillary pumps, all of which have various disadvantages. For example, external syringes and pneumatic pumps are bulky, non-scalable, cannot be miniaturized, and they fundamentally limit the complexity of the PCR system, for example, by limiting the number of external fluidic connections the microfluidic chip can accommodate. Capillary type pumps work on the principle of a fluid filling a set of thin capillaries. Therefore, the pump provides only a single-pass capability. Since the pump is completely passive, the flow of fluid and the number of cycles are "hardwired" into the flow-through chip design and cannot be changed (e.g., through reprogramming). Electrophoretic pumps can require specialized coatings, complex three-dimensional geometries and high operating voltages, which limit the applicability of this type of pump. Other pumps such as peristaltic and rotary pumps have moving parts and are difficult to miniaturize.

In general, therefore, while the use of flow-through microfluidic chips in PCR systems provides some advantages in reducing costs and temperature cycling times, they nevertheless suffer disadvantages with regard to the fundamental need to transport fluid. Fluidic movement is fundamental to essential PCR steps such as sample preparation, mixing components, moving the PCR mixture between different temperature zones, disposing of waste, and so on.

Embodiments of the present disclosure improve on prior fluidic pump solutions in PCR flow-through microfluidic chips, generally through the use of micro-inertial pumps integrated within the PCR microchips. PCR microchips with integrated micropumps enable programmable and flexible cycling protocols, fluid flow paths and fluid flow rates in compact PCR microsystems. Common microfabrication technologies enable large numbers of such micro-inertial pumps to be fabricated on a single PCR microchip (e.g., in the hundreds or thousands). Numerous microfluidic network architectures are suitable for incorporating micro-inertial pumps in microchips that facilitate the PCR process. The integrated micropumps enable large scale parallel PCR processing on a single PCR microchip.

In one example embodiment, a polymerase chain reaction (PCR) system includes a mixture chamber, a denature chamber, an annealing chamber, an extension chamber, and a product chamber, that are fluidically coupled to one another through a plurality of microfluidic channels. An inertial pump is associated with each microfluidic channel, and each inertial pump includes a fluid actuator integrated asymmetrically within its associated microfluidic channel. The fluid actuators are capable of selective activation to circulate fluid between the chambers in a controlled cycle.

In another example embodiment, a PCR system includes a single premixture chamber to provide PCR solution, a plurality of sample chambers to provide sample DNA fragments, a temperature cycling area, and a plurality of mixing chambers. Each mixing chamber is fluidically coupled through microfluidic channels to the single premixture chamber, the temperature cycling area, and to a distinct one of the plurality of sample chambers. The system includes inertial pumps that each have a fluid actuator integrated asymmetrically within a microfluidic channel to pump PCR solution and sample DNA fragments into the mixing chambers, and to pump PCR mixture from the mixing chambers through the temperature cycling area in a controlled cycle. In this embodiment, the system can accept multiple sample DNA fragments to be mixed with the PCR solution in dedicated mixing chambers such that the PCR mixture can be amplified in the temperature cycling area through the PCR process. Thus, different DNA samples can be screened for a particular characteristic in parallel or sequentially, since the microfluidic channels/paths of the different samples do not overlap.

In another example embodiment, the single premixture chamber in the previous embodiment is a plurality of premixture chambers and the plurality of sample chambers is a single sample chamber. Each of the plurality of mixing chambers is fluidically coupled through microfluidic channels to the single sample chamber, the PCR temperature cycling area, and to a distinct one of the premixture chambers. In this embodiment, a single sample DNA fragment can be screened for multiple characteristics.

In another example embodiment, a polymerase chain reaction (PCR) system includes a grid of intersecting microfluidic channels having mixing chambers at each intersection. Premixture chambers are individually coupled to microfluidic channels at a first side of the grid, and sample chambers are individually coupled to microfluidic channels at a second side of the grid. A cleaning agent reservoir is coupled to the grid through secondary microfluidic channels that intersect the grid at cleaning junctions. The system also includes inertial pumps having fluid actuators integrated asymmetrically within microfluidic channels to pump PCR solutions from the premixture chambers into the mixing chambers, sample DNA fragments from the sample chambers into the mixing chambers, PCR mixture from the mixing chambers through a PCR temperature cycling area (i.e., denature area, an annealing area, and an extension area), and cleaning solution from the cleaning agent reservoir through the grid of intersecting microfluidic channels.

ILLUSTRATIVE EMBODIMENTS

FIG. 1 shows a polymerase chain reaction (PCR) system, according to an embodiment of the disclosure. The PCR system 100 includes a PCR microfluidic chip 102, and may also include external fluid reservoirs 104 to supply components of PCR mixtures to the microchip 102. The microchip 102 generally includes chambers or areas for introducing, mixing, and temperature cycling the PCR mixtures (polymerase, dNTPs, template DNA sample, and primers). PCR chambers/areas may contain temperature sensors and heating elements, such as resistive heaters. Microchip 102 also includes microfluidic channels formed between the different chambers or areas to fluidically couple them in a manner that facilitates the proper temperature cycling sequence in the PCR process. Inertial pumps are integrated within the microfluidic channels of microchip 102 to transport PCR solution (i.e., premixture) and template DNA to mixing chambers for mixing into PCR mixtures. The inertial pumps also transport the PCR mixtures between the different temperature chambers or areas (i.e., denaturing, annealing, extending) for temperature cycling, and to product areas when the PCR temperature cycling is complete. In general, the structures and components of the PCR microchip 102 can be fabricated using conventional integrated circuit microfabrication techniques such as electroforming, laser ablation, anisotropic etching, sputtering, dry etching, photolithography, casting, molding, stamping, machining, spin coating and laminating.

The PCR system 100 also includes an electronic controller 106 to control various functional aspects of the PCR processing on microchip 102, such as temperature sensing and control in the reaction chambers/areas, the number of temperature cycles a PCR mixture will undergo, and the direction and rate of flow of the PCR mixture through and between the reaction chambers/areas. Controller 106 typically includes a processor, firmware, software, one or more memory components including volatile and non-volatile memory components, and other electronics for communicating with and controlling components and functions of microchip 102, as well as controlling fluid reservoir(s) 104. Accordingly, electronic controller 106 is a programmable device that typically includes machine-readable instructions (e.g., PCR process instructions 108) in the form of one or more software modules, for example, stored in memory and executable on the controller 106 to control PCR processing on microchip 102. Such modules may include, for example, a temperature sensing and control module 110, a cycle number module 112, a flow direction module 114, and a rate of flow module 116, as shown in the example embodiment of FIG. 1.

Electronic controller 106 may also receive data 118 from a host system, such as a computer, and temporarily store the data 118 in a memory. Typically, data 118 is sent to PCR system 100 along an electronic, infrared, optical, or other information transfer path. Data 118 represents, for example, executable instructions and/or parameters for use alone or in conjunction with other executable instructions in software/firmware modules stored on electronic controller 106 to control fluid flow (e.g., PCR mixture flow), temperature cycling, and other PCR-related functions within microchip 102. For example, various software and data 118 that are executable on programmable controller 106 enable selective and controlled activation of micro-inertial pumps on PCR microchip 102 through precise control over the timing, frequency and duration of compressive and tensile fluid displacements generated by fluid actuators integrated into the microfluidic channels of microchip 102. Readily modifiable (i.e., programmable) control over such fluid actuators through data 118 and/or PCR process instructions 108 executable on controller 106, allows for any number of different PCR cycling protocols that can be performed on embodiments of PCR microchip 102. Such protocols can be readily adjusted on-the-fly for a given microchip 102.

PCR system 100 also typically includes one or more power supplies 120 to provide power to the PCR microchip 102, electronic controller 106, external fluidic reservoirs 104, and other electrical components that may be part of the system 100.

Figure 2:
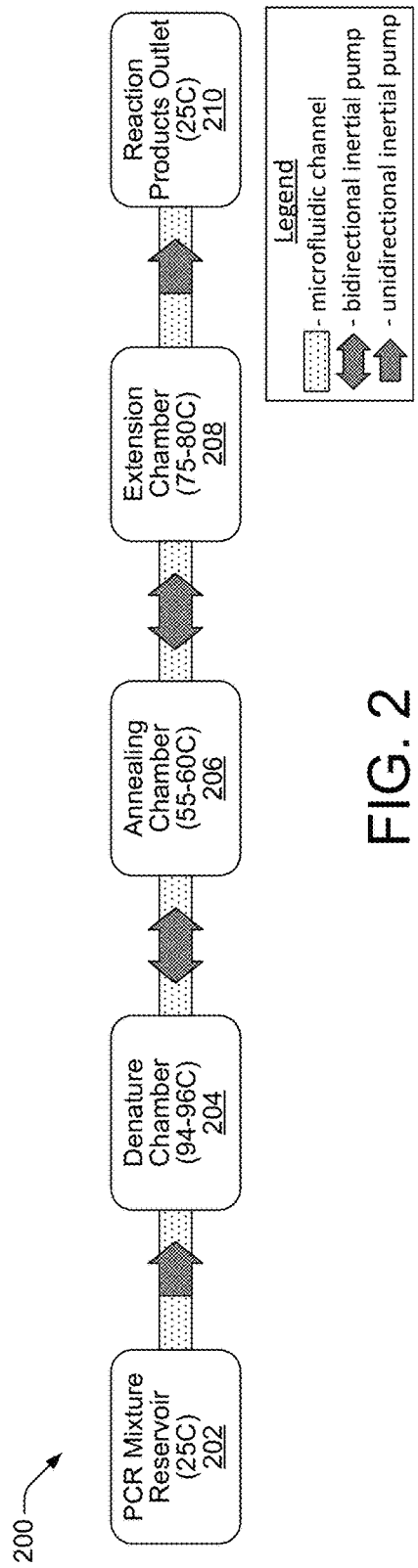
FIG. 2 shows a block diagram of an inertial pump-based, PCR architecture suitable for implementation on a PCR microchip to enable PCR processing, according to an embodiment.

FIG. 2 shows a block diagram of an inertial pump-based, PCR architecture 200 suitable for implementation on a PCR microchip 102 to enable PCR processing, according to an embodiment of the disclosure. The PCR architecture 200 is a functionally if not physically, linear microfluidic network that includes a PCR mixture reservoir 202, denature chamber 204, annealing chamber 206, extension chamber 208, and product outlet chamber 210, coupled together in a linear fashion by microfluidic channels. Each microfluidic channel includes, or is part of, an inertial pump configured to move fluidic PCR mixture between chambers in the linear architecture 200. The inertial pumps in the linear architecture 200 can be bidirectional pumps, or, as shown in the FIG. 2 example, they can be unidirectional pumps such as the unidirectional inertial pumps between the mixture reservoir 202 and denature chamber 204, and between the extension chamber 208 and outlet chamber 210. The pumps in FIG. 2 are shown in this manner in order to better illustrate the typical flow of the PCR mixture through the microfluidic channels of the linear architecture 200 as discussed below. The operation of both unidirectional and bidirectional micro-inertial pumps discussed throughout this disclosure is based on the asymmetric integration (placement) of fluid actuators within the microfluidic channels, as well as the generation by those fluid actuators of compressive and tensile fluid displacements whose durations are asymmetric (i.e., not equal). The operation of the unidirectional and bidirectional inertial pumps in this regard is discussed in detail herein below.

In the linear PCR architecture 200, the known PCR process can be implemented by repeated cycling of PCR mixture through the different temperatures of the denature 204, annealing 206 and extension 208 chambers. The amount of time and the temperatures illustrated and discussed herein regarding the different PCR reaction chambers are intended as examples only. Therefore, while the times and temperatures are thought to be generally accurate for implementing the known PCR process, they may vary. Indeed, as noted above, the described embodiments contemplate and enable programmable control over these and other factors in a PCR process implemented on a PCR microchip 102. Temperature sensing and temperature control within the different PCR chambers/areas is discussed below with respect to FIG. 4.

In the linear PCR architecture 200, a PCR process can begin when the PCR mixture reservoir 202 receives PCR mixture (polymerase, dNTPs, template DNA sample, and primers), such as from external reservoir 104, for example. The PCR mixture reservoir is typically maintained at an ambient temperature of approximately 25° C. (degrees centigrade). The PCR mixture moves from the PCR mixture reservoir 202 through a microfluidic channel to the denature chamber 204 by the pumping operation of a unidirectional (or bidirectional) inertial pump. The temperature of the denature chamber 204 is maintained between approximately 94-96° C., and the PCR mixture remains in the denature chamber 204 at temperature for approximately 1 minute. In the denature chamber 204, coiled DNA strands (i.e., of the DNA sample template) separate to form single strands. The PCR mixture then moves from the denature chamber 204 through a microfluidic channel to the annealing chamber 206 by the pumping operation of a bidirectional inertial pump. The temperature of the annealing chamber 206 is maintained between approximately 55-60° C., and the PCR mixture remains in the annealing chamber 206 at temperature for approximately 1 minute. In the annealing chamber 206, primers recognize or target DNA fragments of interest and bind to both the DNA and complementary strands at annealing sites which identify these DNA fragments. This prepares the targeted DNA fragments for DNA synthesis in the extension phase. The PCR mixture then moves from the annealing chamber 206 through a microfluidic channel to the extension chamber 208 by the pumping operation of a bidirectional pump. The temperature of the extension chamber 208 is maintained between approximately 75-80° C., and the PCR mixture remains in the extension chamber 208 at temperature for approximately 1 minute. In the extension chamber 208, polymerase activates to perform DNA synthesis on the targeted fragments using nucleotides as building blocks.

When the extension chamber 208 reaction is complete, the PCR mixture has undergone one PCR temperature cycle, which theoretically has doubled the number of targeted DNA fragments. This cycle can then be repeated to generate an exponential growth in the concentration of the targeted DNA fragment. In the linear PCR architecture 200 of FIG. 2, this cycle is repeatable by controlling the bidirectional inertial pumps deployed between the denature 204, annealing 206 and extension 208 chambers. More specifically, a programmable controller 106 is configured to execute instructions from a flow direction module 114, for example, to control the bidirectional pumps such that they move the PCR mixture in an opposite direction from the extension chamber 208 back through the annealing chamber 206 and to the denature chamber 204, where the PCR temperature cycling process begins again. Additional instructions executable on controller 106 from a cycle number module 112, for example, direct the controller 106 to cycle the bidirectional pumps a particular number of times so that the PCR mixture undergoes a desired number of temperature cycles. Thus, temperature cycling in the linear PCR architecture 200 of FIG. 2 proceeds in a back-and-forth, linear manner as the PCR mixture is pumped back and forth between the three PCR reaction chambers (i.e., the denature, annealing and extension chambers). The number of cycles can be flexibly controlled by programmable controller 106 to achieve the desired DNA amplification results. When the programmed number of cycles has been completed, the PCR mixture then moves from the extension chamber 208 through a microfluidic channel to a reaction product outlet chamber 210 by the pumping operation of a unidirectional (or bidirectional) pump. The product outlet chamber 210 is typically maintained at an ambient temperature such of approximately 25° C.

The PCR temperature cycling process described above with regard to the linear PCR architecture 200 of FIG. 2 is generally applicable to the various embodiments of PCR architectures discussed herein, and will therefore not be discussed in detail with respect to such other embodiments.

Figure 3:
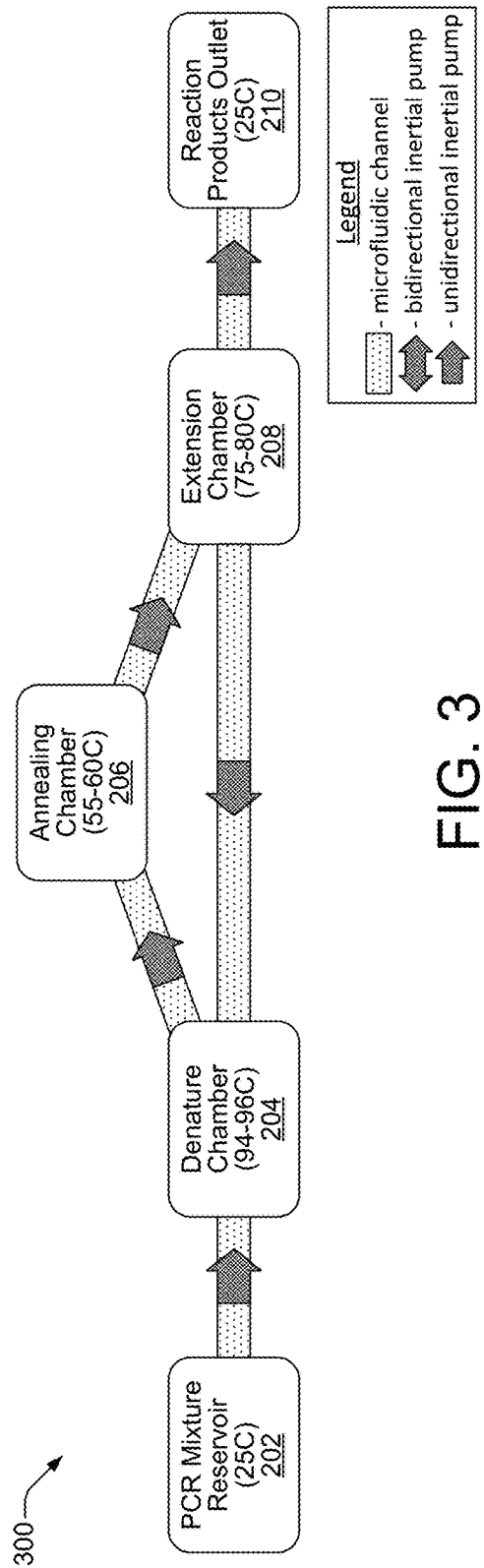
FIG. 3 shows a block diagram of another inertial pump-based, PCR architecture suitable for implementation on a PCR microchip to enable PCR processing, according to an embodiment.

FIG. 3 shows a block diagram of an inertial pump-based, PCR architecture 300 suitable for implementation on a PCR microchip 102 to enable PCR processing, according to an embodiment of the disclosure. The PCR architecture 300 is a circular microfluidic network in which the three PCR reaction chambers (i.e., the denature 204, annealing 206 and extension 208 chambers) are fluidically coupled in a circular fashion by microfluidic channels. Each microfluidic channel includes, or is part of, an inertial pump configured to move fluidic PCR mixture between chambers in the circular architecture 300. In this architecture 300, the inertial pumps are all shown as unidirectional pumps. However, the inertial pumps could also be bidirectional pumps. The pumps are shown as unidirectional pumps in order to better illustrate the typical flow of the PCR mixture through the microfluidic channels of the circular architecture 300. That is, PCR mixture moves (i.e., is pumped) from the PCR mixture reservoir 202 to the denature chamber 204, then to the annealing chamber 206, and then to the extension chamber 208. The PCR mixture is then either pumped back to the denature chamber 204 for additional temperature cycling, or it is pumped to the product output chamber 210. Thus, to accomplish typical PCR temperature cycling processing in the circular architecture 300, the use of unidirectional inertial pumps is sufficient, but not required.

Figure 4:
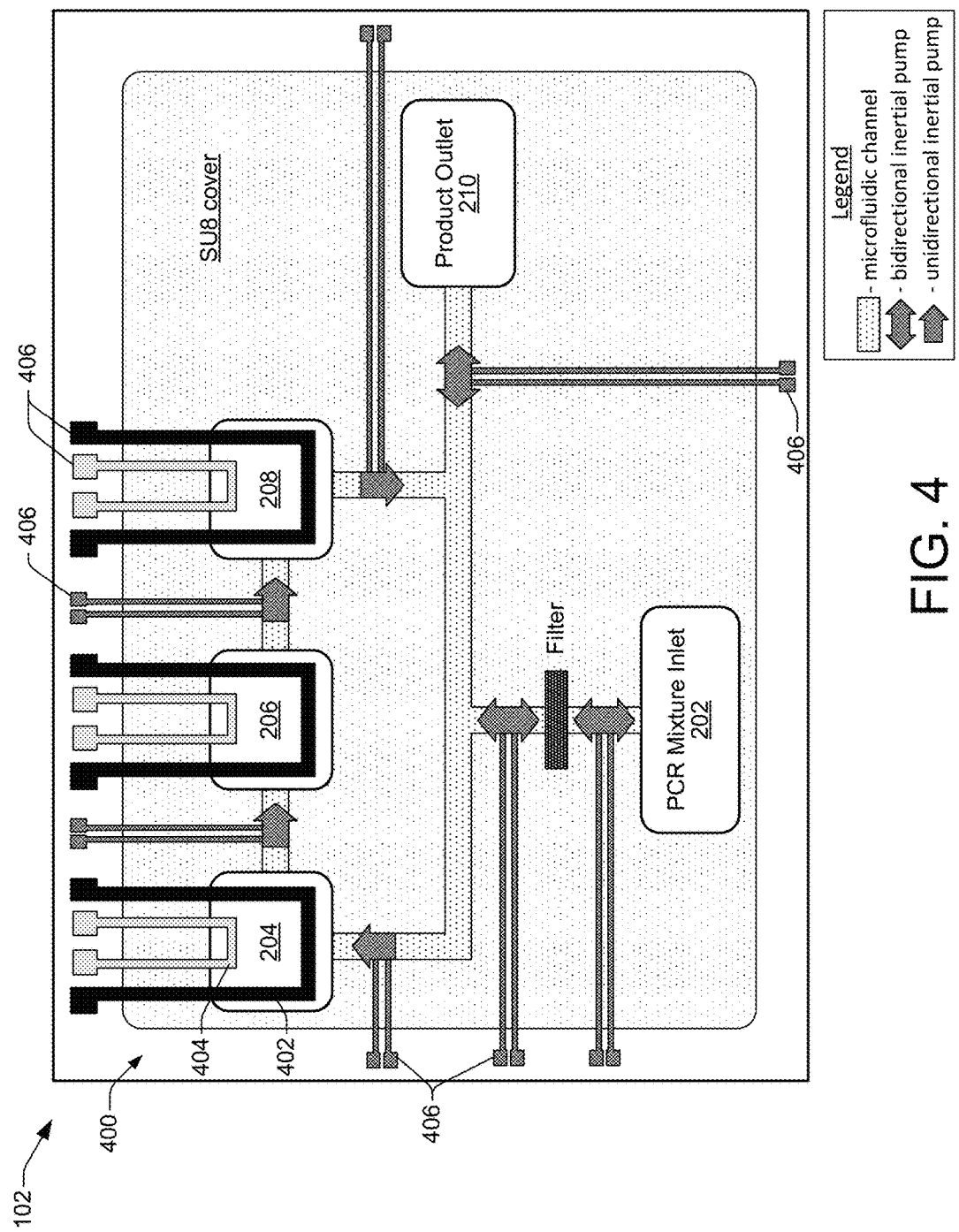
FIG. 4 shows an example microchip layout of an inertial pump-based, PCR architecture suitable for implementation on a PCR microchip to enable PCR processing, according to an embodiment.

FIG. 4 shows an example microchip layout of an inertial pump-based, PCR architecture 400 suitable for implementation on a PCR microchip 102 to enable PCR processing, according to an embodiment of the disclosure. The PCR architecture 400 is a circular architecture 400 such as that shown in the block diagram of FIG. 3. Accordingly, the PCR architecture 400 facilitates the typical flow of PCR mixture as it cycles between PCR reaction chambers through the microfluidic channels, from the PCR mixture reservoir 202 to the denature chamber 204, from the denature chamber 204 to the annealing chamber 206, from the annealing chamber 206 to the extension chamber 208, and then from the extension chamber 208 back to the denature chamber 204, where the cycle begins again. The temperature cycling continues until a preprogrammed number of temperature cycles has been completed, after which the PCR mixture moves from the extension chamber 208 to the product output chamber 210.

In addition to showing the microfluidic channels and inertial pumps, the example layout of the PCR architecture 400 also shows resistive heaters 402 and temperature sensors 404 in the PCR reaction chambers, as well as electrodes 406 for energizing the heaters 402, sensors 404 and inertial pumps. In some embodiments, resistive heating elements 402 can also function as temperature sensors when implemented, for example, as thermistors or resistive thermal devices. In such embodiments, separate temperature sensors would not be needed. As noted above, electronic controller 106 controls various functional aspects of the PCR processing on microchip 102, including temperature sensing and control within the reaction chambers/areas. During the temperature cycling process as the controller 106 manages the inertial pumps to move PCR mixture between the PCR reaction chambers, it also maintains the temperatures of the PCR reaction chambers (i.e., the denature 204, annealing 206 and extension 208 chambers) so that they remain within a specified range that facilitates the PCR amplification process. More specifically, the programmable controller 106 is configured to execute instructions from a temperature sensing and control module 110, for example, which enables the controller 106 to monitor the temperature in each chamber through temperature sensors 406. The controller 106 compares the sensed temperatures to expected temperatures for the different PCR reaction chambers, and if necessary, in response to the comparisons it adjusts the temperatures to appropriate, programmed, values by selectively energizing resistive heating elements 402.

The example layout of the PCR architecture 400 of FIG. 4 additionally provides a general indication about the fabrication of an inertial pump-based, PCR architecture on a microchip 102. As previously noted, the structures and components of the PCR microchip 102 can be fabricated using conventional integrated circuit microfabrication techniques such as electroforming, laser ablation, anisotropic etching, sputtering, dry etching, photolithography, casting, molding, stamping, machining, spin coating and laminating. In general, the resistive elements 402, temperature sensors 404, electrodes 406, and inertial pumps can be fabricated on an underlying substrate (e.g., silicon). A channel or chamber layer can then be applied over the substrate, in which the microfluidic channels and PCR chambers can be formed (i.e., PCR mixture chamber 202, denature chamber 204, annealing chamber 206, extension chamber 208, and product chamber 210). A top layer can then be applied over the channel/chamber layer. Both the chamber layer and top layer can be formed, for example, of a transparent SU8 material commonly used as a photoresist mask for fabrication of semiconductor devices.

Figure 5A:
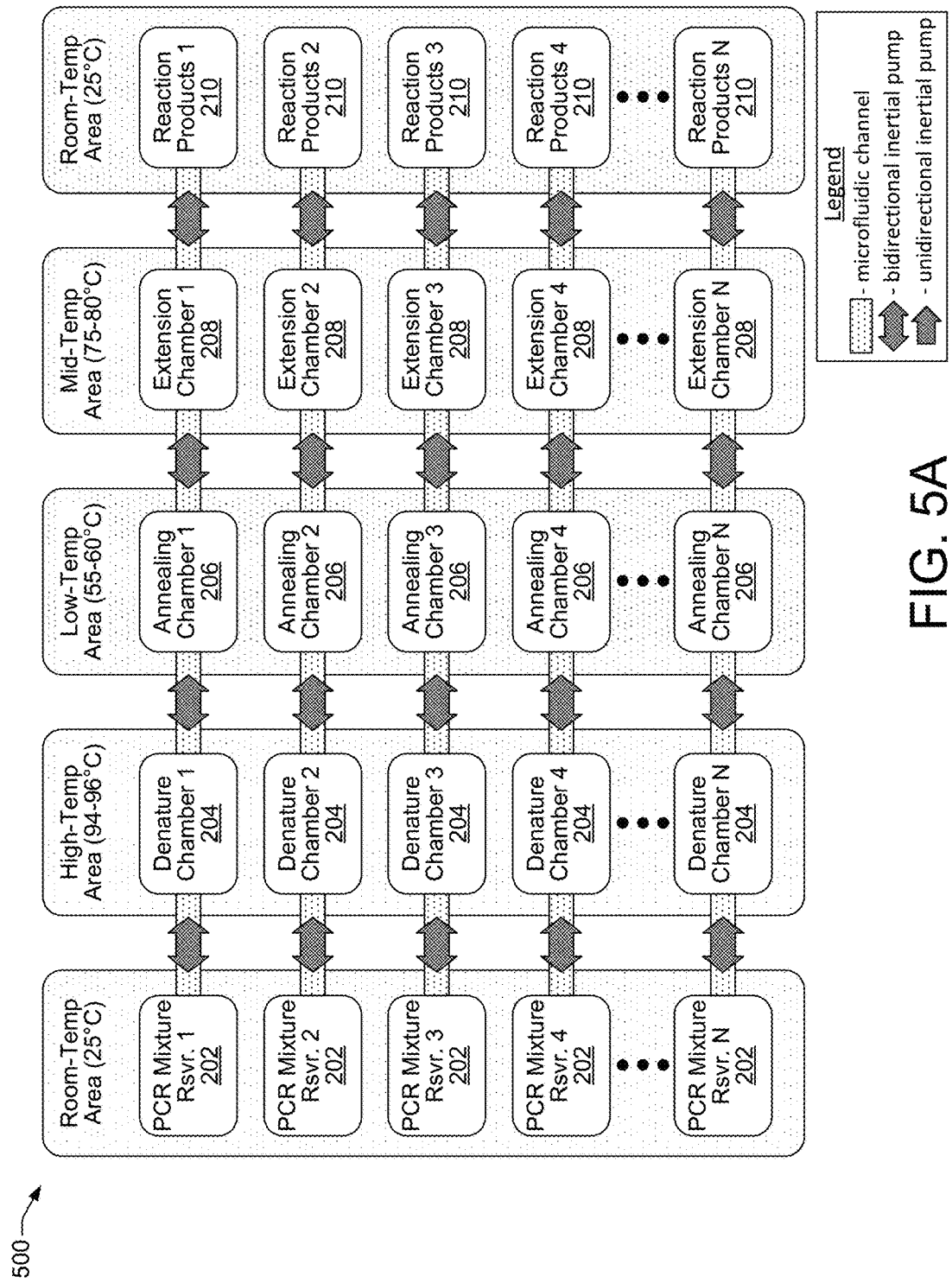
FIG. 5A shows a parallel, linear-type, inertial pump-based, PCR architecture suitable for implementation on a PCR microchip, according to an embodiment.
Figure 5B:
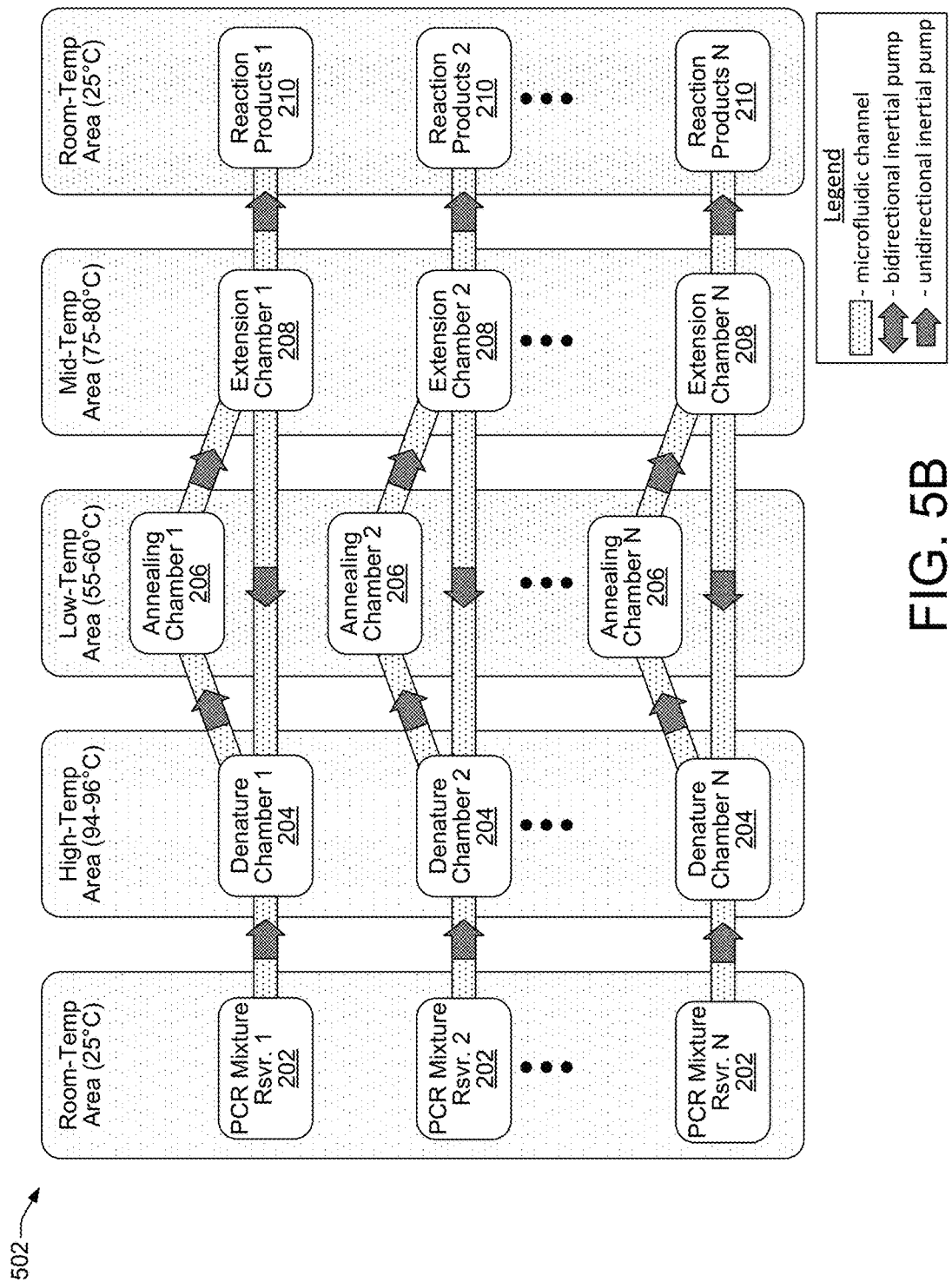
FIG. 5B shows a parallel, circular-type, inertial pump-based, PCR architecture suitable for implementation on a PCR microchip, according to an embodiment.
Figure 7:
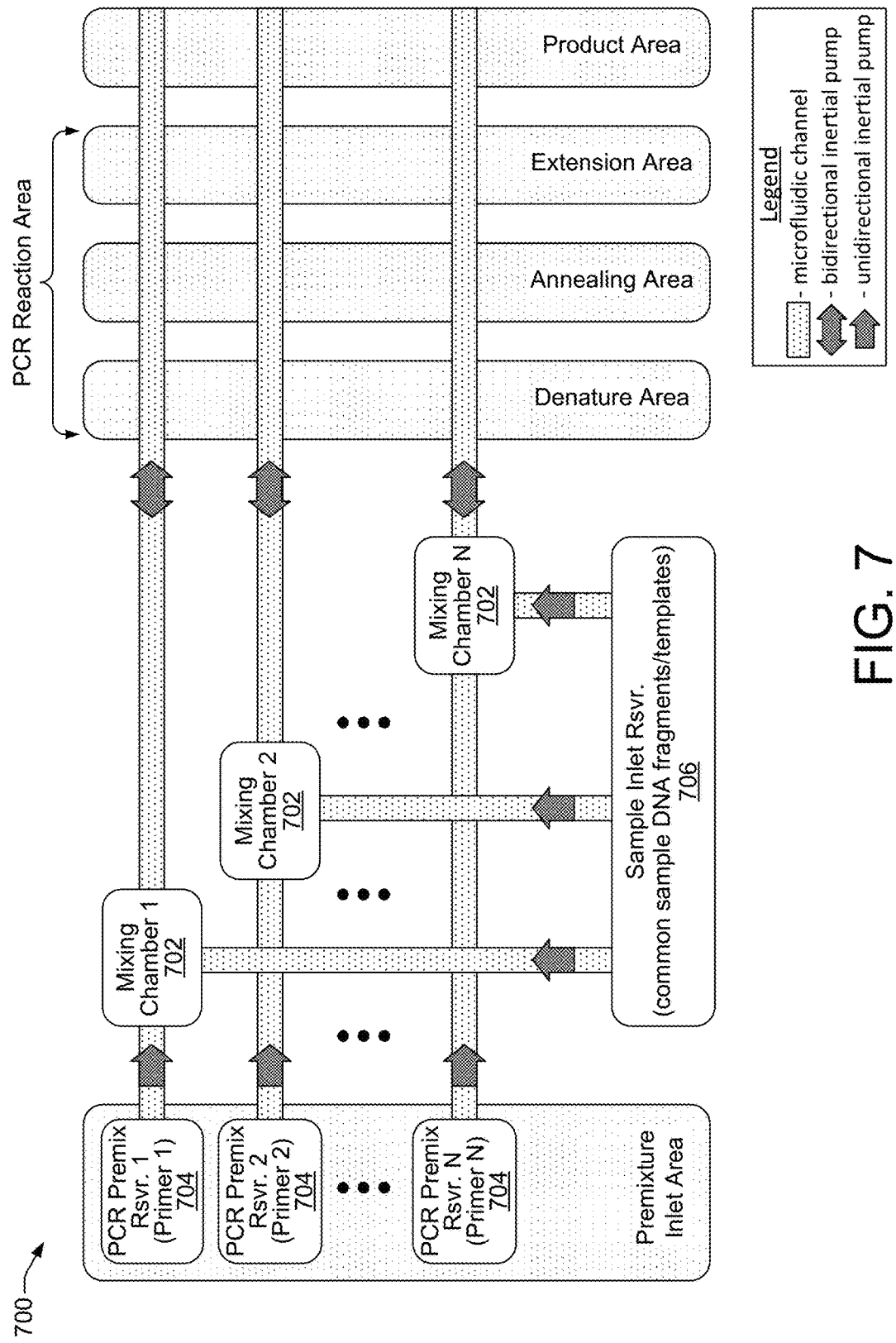
FIG. 7 shows another parallel, linear-type, inertial pump-based, PCR architecture that includes dedicated mixing chambers suitable for implementation on a PCR microchip, according to an embodiment.
Figure 8:
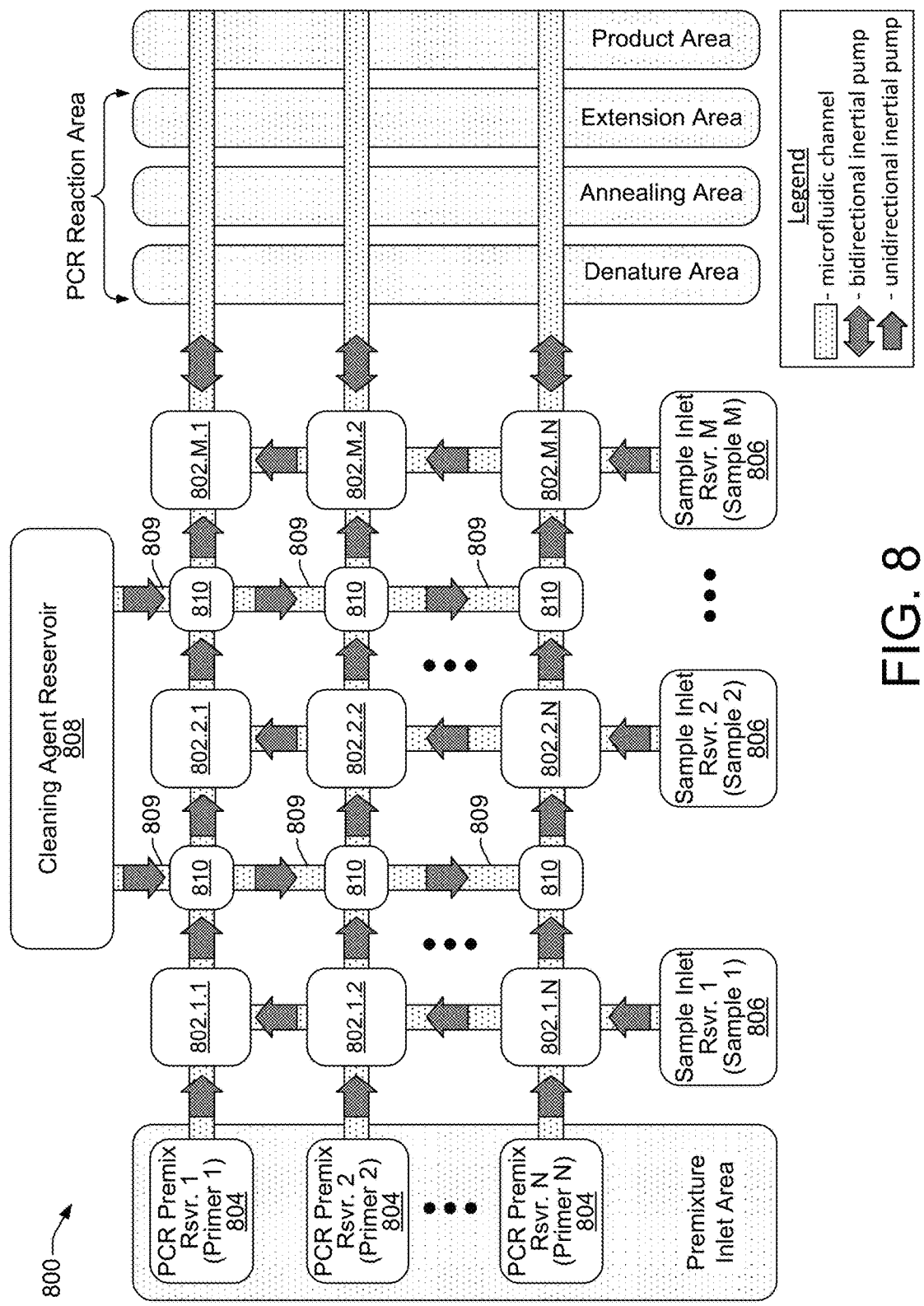
FIG. 8 shows a parallel, grid-type, inertial pump-based, PCR architecture that includes shared mixing chambers and a cleaning system, suitable for implementation on a PCR microchip, according to an embodiment.

Integrating micro-inertial pumps into microfluidic channels on a microchip 102 enables the parallelization of the PCR process on a massive scale. FIGS. 5-8 show examples of parallelized, inertial pump-based, PCR architectures suitable for implementation on a PCR microchip 102 to enable parallel PCR processing, according to different embodiments. FIG. 5A shows a parallel, linear-type, inertial pump-based, PCR architecture 500 that is similar to the linear architecture discussed above with regard to FIG. 2, but which is duplicated N>>1 times, according to an embodiment of the disclosure. FIG. 5B shows a parallel, circular-type, inertial pump-based, PCR architecture 502 that is similar to the circular architecture discussed above with regard to FIG. 3, but which is duplicated N>>1 times, according to an embodiment of the disclosure. It is noted that while the additional parallel embodiments of FIGS. 6-8 show only linear-type, inertial pump-based, PCR architectures, corresponding circular-type architectures for these embodiments are both possible and contemplated by this disclosure, similar to the circular-type architecture explicitly shown in FIG. 5B.

Referring now to FIGS. 5A and 5B, the parallel PCR architectures 500 and 502 are suitable for implementation on a microchip 102, and when coupled with the programmable control of a controller 106 they enable virtually unlimited options for PCR processing. For example, in the parallel linear PCR architectures 500 and 502, the PCR mixtures in the N PCR mixture reservoirs 202 can all have different sample DNA templates and different primers, and all the amplification reactions can proceed in parallel. Thus, multiple different DNA samples (i.e., people) can be screened for a particular gene, one sample can be screened for numerous different genes, several different samples can be screened for numerous different genes, and so on. The PCR processing scenarios enabled by these parallel architectures 500 and 502 are increased to an even greater degree by the flexibility in temperature cycling protocols that can be readily programmed into and implemented by controller 106. For example, controller 106 can implement different cycling protocols with respect to each of the N linear PCR processes proceeding in parallel in architectures 500 and 502 such that each process has a different number of temperature cycles, a different mixture flow rate, different amounts of time per PCR reaction chamber, and different temperatures within the PCR reaction chambers.

FIG. 6 shows a parallel, linear-type, inertial pump-based, PCR architecture 600 that includes dedicated mixing chambers and is suitable for implementation on a PCR microchip 102, according to an embodiment of the disclosure. In this example, N multiple mixing chambers 602 enable independent mixing of a common PCR premixture solution with different sample DNA fragments for parallel PCR processing along N linear PCR reaction paths. The parallel PCR architecture 600 includes a single PCR premixture reservoir 604 in a premixture inlet area to receive a PCR premixture solution (e.g., from an external reservoir 104) that does not include a sample DNA fragment/template. The PCR solution received in premixture reservoir 604 therefore includes polymerase, dNTPs, and primers, but no sample DNA fragment. The parallel PCR architecture 600 includes N multiple sample DNA inlet reservoirs 606 corresponding with the N mixing chambers 602, each capable of receiving a sample DNA fragment. Each of the multiple mixing chambers 602 is fluidically coupled to a distinct sample reservoir 606 and to the single PCR premixture reservoir 604 through microfluidic channels.

Microfluidic channels in the parallel PCR architecture 600, as in the previously discussed embodiments, include integrated fluid actuators that are asymmetrically located within the channels to form integrated micro-inertial pumps. The inertial pumps can be bidirectional and sometimes unidirectional, and the integrated fluid actuator of each inertial pump is individually controllable (e.g., by a controller 106) to generate compressive and tensile fluid displacements having asymmetric (i.e., unequal) durations that move and circulate fluid between different chambers or areas of the parallel PCR architecture 600. The control of inertial pumps in the parallel PCR architecture 600 can be implemented through instruction modules executable on controller 106. For example, controller 106 can execute various instruction modules (e.g., temperature sense and control module 110, cycle number module 112, flow direction module 114, flow rate module 116) to implement different PCR temperature cycling protocols with respect to each of the N linear PCR processes proceeding in parallel in architecture 600 such that each process has a different number of temperature cycles, a different flow rate, different amounts of time per PCR reaction area/chamber, and different temperatures within the PCR reaction areas/chambers.

In the parallel PCR architecture 600, examples of unidirectional inertial pumps are those shown between PCR premixture reservoir 604 and mixing chambers 602 that move PCR solution from the PCR premixture reservoir 604 to the chambers 602, and those shown between sample DNA inlet reservoirs 606 and mixing chambers 602 that move fluidic sample DNA templates from the sample inlet reservoirs 606 to the chambers 602. Examples of bidirectional inertial pumps are those shown between the mixing chambers 602 and the PCR reaction area. These bidirectional inertial pumps move PCR mixtures (i.e., PCR solution after it has been mixed with a sample DNA fragment/template) from the mixing chambers 602 to the PCR reaction area, and then back and forth between the denature, annealing and extension areas (during PCR temperature cycling), and then on to the reaction product area after the temperature cycling is complete. Although not illustrated, the denature, annealing, extension and product areas may include specific denature, annealing, extension and product chambers along each of the respective microfluidic channels. In addition, there may also be additional bidirectional inertial pumps in between each of the denature, annealing and extension areas to facilitate fluidic movement between these different reaction areas.

In the parallel PCR architecture 600, the sample DNA fragments (DNA templates) provided at sample inlet reservoirs 606 can all be different, or they can be common, or they can be some combination thereof. Mixing the common PCR premixture solution with multiple different samples in dedicated mixing chambers 602 of architecture 600 enables, for example, the screening of multiple different patients for the presence of a particular gene, such as a flu virus. The use of common samples in a number of different sample inlet reservoirs 606 enables multiple parallel screening of the same sample (i.e., the same patient), which can be a useful technique for reducing screening errors.

FIG. 7 shows another parallel, linear-type, inertial pump-based, PCR architecture 700 that includes dedicated mixing chambers suitable for implementation on a PCR microchip 102, according to an embodiment of the disclosure. In this example, N multiple mixing chambers 702 enable independent mixing of different PCR premixture solutions with common sample DNA fragments for parallel PCR processing along N linear PCR reaction paths. In this example, multiple PCR premixture reservoirs 704 in a premixture inlet area can receive multiple PCR premixture solutions (e.g., from an external reservoir 104) that do not include a sample DNA fragment, or template. The PCR solutions received in premixture reservoirs 704 therefore includes polymerase, dNTPs, and different primers (e.g., primers 1, 2, . . . , N), but no sample DNA fragments. The parallel PCR architecture 700 includes a single sample DNA inlet reservoir 706 capable of receiving a sample DNA fragment. Each of the multiple mixing chambers 702 is fluidically coupled to a distinct PCR premixture reservoir 704 and to the single sample reservoir 706 through microfluidic channels.

Similar to the architectures discussed above (e.g., architectures 200, 300, 500, 600), microfluidic channels in the parallel PCR architecture 700 include integrated fluid actuators that are asymmetrically located within the channels to form integrated micro-inertial pumps. The inertial pumps can be bidirectional and sometimes unidirectional, and the integrated fluid actuator of each inertial pump is individually controllable (e.g., by a controller 106) to generate compressive and tensile fluid displacements having asymmetric (i.e., unequal) durations that move and circulate fluid between different chambers or areas of the parallel PCR architecture 700. The control of inertial pumps in the parallel PCR architecture 700 can be implemented through instruction modules executable on controller 106. For example, controller 106 can execute various instruction modules (e.g., temperature sense and control module 110, cycle number module 112, flow direction module 114, flow rate module 116) to implement different PCR temperature cycling protocols with respect to each of the N linear PCR processes proceeding in parallel in architecture 700 such that each process has a different number of temperature cycles, a different flow rate, different amounts of time per PCR reaction area/chamber, and different temperatures within the PCR reaction areas/chambers.

In the parallel PCR architecture 700, examples of unidirectional inertial pumps are those shown between PCR premixture reservoirs 704 and mixing chambers 702 that move PCR solutions from the PCR premixture reservoirs 704 to the chambers 702, and those shown between the sample DNA inlet reservoir 706 and mixing chambers 702 that move a common fluidic sample DNA fragment/template from the sample inlet reservoir 706 to the chambers 702. Examples of bidirectional inertial pumps are those shown between the mixing chambers 702 and the PCR reaction area. These bidirectional inertial pumps move PCR mixtures (i.e., PCR solutions that have been mixed with a sample DNA fragment/template) from the mixing chambers 702 to the PCR reaction area, and then back and forth between the denature, annealing and extension areas (during PCR temperature cycling), and then on to the reaction product area after the temperature cycling is complete. Although not illustrated, the denature, annealing, extension and product areas may include specific denature, annealing, extension and product chambers along each of the respective microfluidic channels. In addition, there may also be additional bidirectional inertial pumps in between each of the denature, annealing and extension areas to facilitate fluidic movement between these different reaction areas.

In the parallel PCR architecture 700, the PCR solutions from the PCR premixture reservoirs 704 can all have different primers (e.g., primers 1, 2, . . . , N), or the primers can be common, or they can be some combination thereof. Mixing the different PCR solutions (i.e., with different primers) with common sample DNA fragments in dedicated mixing chambers 702 of architecture 700 enables, for example, screening a patient for the presence of multiple different genes. The use of common PCR solutions (i.e., with common primers) in PCR in a number of the PCR premixture reservoirs 704 enables multiple parallel screenings of the common sample (i.e., the single patient), which can be useful for reducing screening errors.

FIG. 8 shows a parallel, grid-type, inertial pump-based, PCR architecture 800 that includes shared mixing chambers and a cleaning system, suitable for implementation on a PCR microchip 102, according to an embodiment of the disclosure. In this example, (M×N) mixing chambers 802 (i.e., 802.1.1-802.M.N) serve as intersections in a functional grid that couples M sample DNA inlet reservoirs 806 with N PCR premixture reservoirs 804 through microfluidic channels. The N PCR premixture reservoirs 804 are fluidically coupled to microfluidic channels at one side of the grid, while the M sample DNA inlet reservoirs 806 are fluidically coupled to microfluidic channels at another (orthogonal) side of the grid. In the parallel PCR architecture 800, any one of M samples can be mixed with any of N PCR premixture solutions through a mixing chamber 802, and subsequently temperature cycled through the PCR reaction area for amplification. Thus, all M samples can be screened for N different genes or DNA fragments.

In the parallel PCR architecture 800, because the microfluidic channels and mixing chambers 802 are shared between different samples and PCR solutions (with different primers), the entire microfluidic network is to be cleaned between successive screenings. Cleaning is implemented by a cleaning system that includes a cleaning agent reservoir 808 fluidically coupled to the architecture 800 through a secondary group of microfluidic channels 809 and cleaning junctions 810. As shown in FIG. 8, micro-inertial pumps in secondary microfluidic channels 809 between the cleaning agent reservoir 808 and the cleaning junctions 810 pump cleaning agent from the reservoir 808 through the cleaning junctions 810. Inertial pumps on the grid architecture 800 then operate to distribute the cleaning agent further through channels and chambers throughout the grid architecture 800 to flush out remaining PCR mixture that may be left over from previous PCR processes. In this manner, a microchip 102 that includes the parallel architecture 800 can therefore be used over and over again, and is suitable for integration into a PCR system that performs automated PCR processing. Automated processing can proceed, for example, in a sequence beginning with processing a sample 1, cleaning the architecture 800, processing a sample 2, cleaning the architecture 800, and so on.

Similar to the architectures discussed above (e.g., architectures 200, 300, 500, 600, 700), microfluidic channels in the parallel PCR architecture 800 include integrated fluid actuators that are asymmetrically located within the channels to form integrated micro-inertial pumps. The inertial pumps can be bidirectional and sometimes unidirectional as shown in FIG. 8, and the integrated fluid actuator of each inertial pump is individually controllable (e.g., by a controller 106) to generate compressive and tensile fluid displacements having asymmetric (i.e., unequal) durations that move and circulate fluid between different chambers, areas, and junctions of the parallel PCR architecture 800. The control of inertial pumps in the parallel PCR architecture 800 is implemented and controlled in a similar manner as discussed above with regard to other embodiments. Thus, controller 106 executes various instruction modules (e.g., temperature sense and control module 110, cycle number module 112, flow direction module 114, flow rate module 116) to implement different PCR temperature cycling protocols. For the PCR architecture 800, one of such PCR temperature cycling protocols includes a cleaning routine that controls appropriate inertial pumps to circulate cleaning agent from the cleaning agent reservoir 808 through the architecture 800.

Bidirectional and unidirectional inertial pumps in the parallel PCR architecture 800 work in the same general manner as noted above with regard to other architectures to move PCR premixtures and samples into mixing chambers 802, and then back and forth between the denature, annealing and extension areas (during PCR temperature cycling), and on to the reaction product area after the temperature cycling is complete. Although not illustrated, the denature, annealing, extension and product areas in architecture 800 may include specific denature, annealing, extension and product chambers along each of the respective microfluidic channels. In addition, there may also be bidirectional inertial pumps in between each of the denature, annealing and extension areas to facilitate fluidic movement between these different reaction areas.

Inertial Pumps

As noted above, the operation of both unidirectional and bidirectional micro-inertial pumps in PCR architectures discussed throughout this disclosure is based on the asymmetric integration (placement) of fluid actuators within the microfluidic channels, as well as the generation by those fluid actuators of compressive and tensile fluid displacements whose durations are asymmetric (i.e., not equal). Fluid actuators integrated within microfluidic channels at asymmetric locations (i.e., toward the ends of the channels) can generate both unidirectional and bidirectional fluid flow through the channels. Selective activation of multiple fluid actuators located asymmetrically toward the ends of multiple microfluidic channels in a network architecture enables the generation of directionally-controlled fluid flow patterns within the network. In addition, temporal control over the mechanical operation or motion of a fluid actuator enables directional control of fluid flow through a fluidic network channel. Thus, precise control over the forward and reverse strokes (i.e., compressive and tensile fluid displacements) of a single fluid actuator can provide bidirectional fluid flow within a microfluidic network channel to generate directionally-controlled fluid flow patterns within the network.

Fluid actuators can be driven by a variety of actuator mechanisms such as thermal bubble resistor actuators, piezo membrane actuators, electrostatic (MEMS) membrane actuators, mechanical/impact driven membrane actuators, voice coil actuators, magneto-strictive drive actuators, and so on. The fluid actuators and other structures and components of PCR architectures (e.g., PCR reaction chambers, microfluidic channels, etc.) on a PCR microchip 102 can be fabricated using conventional integrated circuit microfabrication techniques such as electroforming, laser ablation, anisotropic etching, sputtering, dry etching, photolithography, casting, molding, stamping, machining, spin coating and laminating.

Figure 9:
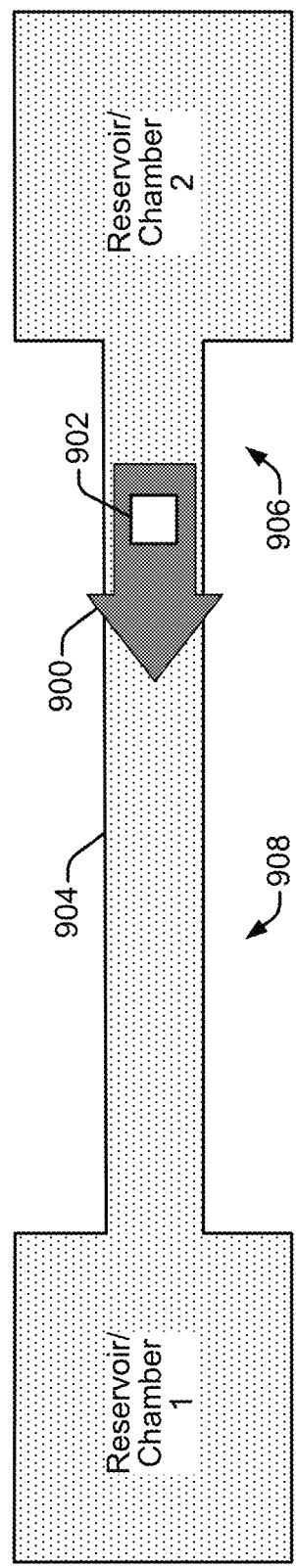
FIG. 9 shows an inertial pump integrated in a microfluidic channel that is suitable for implementing in a PCR architecture of a PCR microchip, according to an embodiment.

FIG. 9 shows an inertial pump integrated in a microfluidic channel that is suitable for implementing in a PCR architecture of a PCR microchip 102, according to an embodiment of the disclosure. Referring generally to FIG. 9, the pumping effect of an inertial pump 900 is based on the action (i.e., fluid displacements) of a fluid actuator 902 located asymmetrically within a fluidic channel 904 (e.g., a microfluidic channel) whose width is narrower than the width of the reservoir or chamber from, or to, which fluid is being pumped. The asymmetric placement of the fluid actuator 902 to one side of the center point of a fluidic channel 904 establishes a short side 906 of the channel and a long side 908 of the channel. Depending on the type of fluid actuator mechanism deployed (see discussion of FIGS. 10-17 below), a unidirectional fluid flow can be achieved in the direction from the short side 906 (i.e., where the fluid actuator is located) to the long side 908 of the channel. A fluid actuator 902 placed symmetrically within a fluidic channel 904 (i.e., at the center of the channel) will generate zero or close to zero net flow. Thus, the asymmetric placement of the fluid actuator 902 within the fluidic channel 904 is one condition that needs to be met in order for an inertial pump 900 to achieve a pumping effect that can generate a net fluid flow through the channel.

However, in addition to the asymmetric placement of the fluid actuator 902 within the fluidic channel 904, another component of the pumping effect of an inertial pump 900 is the manner of operation of the fluid actuator 902. Specifically, to achieve the pumping effect and a net fluid flow through the channel 904, the fluid actuator 902 should also operate asymmetrically with respect to its displacement of fluid within the channel. During operation, a fluid actuator 902 in a fluidic channel 904 deflects, first in one direction and then the other (such as the up and down deflections of a flexible membrane or a piston stroke), to cause fluid displacements within the channel. In general, a fluid actuator 902 generates a wave propagating in the fluidic channel 904 that pushes fluid in two opposite directions along the channel. If the operation of the fluid actuator 902 is such that its deflections displace fluid in both directions with the same speed, then the fluid actuator 902 will generate zero or near zero net fluid flow in the channel 904. Therefore, in order to generate net fluid flow, the operation of the fluid actuator 902 should be configured so that its deflections, or fluid displacements, are not temporally symmetric. That is, an upward deflection into the fluidic channel causing a compressive fluid displacement should not be the same duration as the subsequent downward deflection causing a tensile fluid displacement. Thus, an asymmetric operation of the fluid actuator with respect to the timing of its deflection strokes, or fluid displacements, is a second condition that needs to be met in order for an inertial pump 900 to achieve a pumping effect that can generate a net fluid flow through the channel 904.

Figure 10:
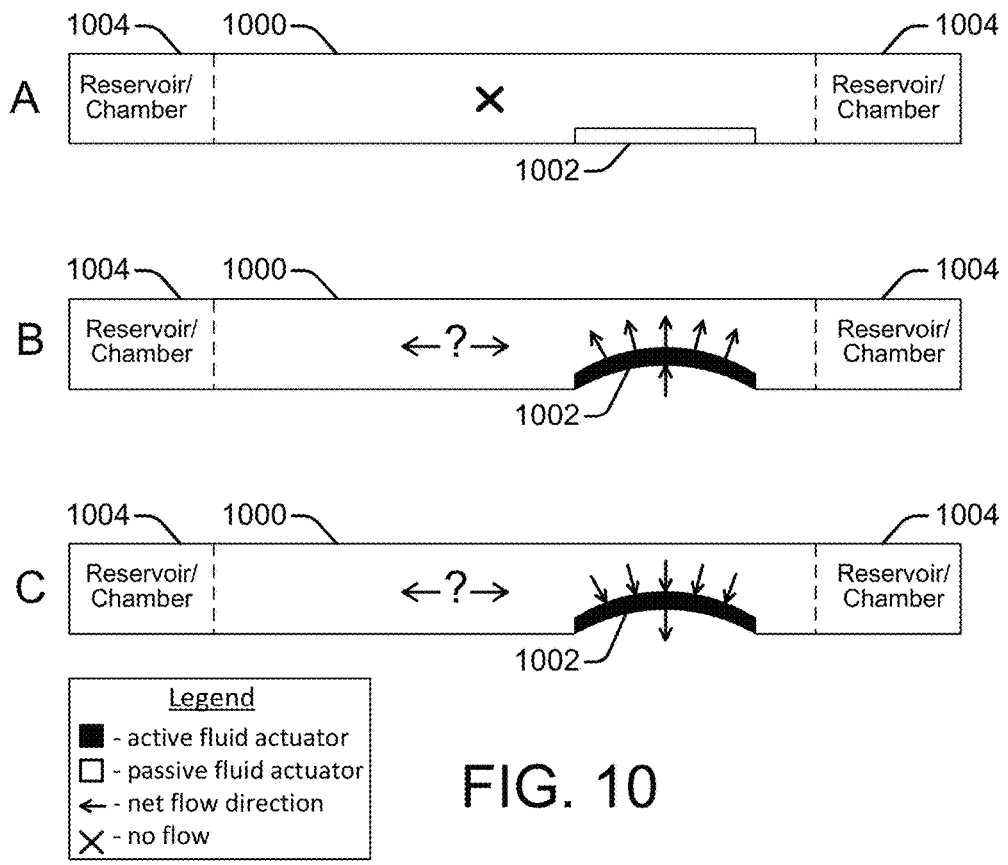
FIG. 10 shows a side view of a microfluidic channel with an integrated inertial pump whose fluid actuator is in different stages of operation, according to an embodiment.

FIG. 10 shows a side view of a microfluidic channel 1000 with an integrated inertial pump whose fluid actuator 1002 is in different stages of operation, according to an embodiment of the disclosure. Fluidic reservoirs or chambers 1004 are connected at each end of the channel 1000. The integrated fluid actuator 1002 is asymmetrically placed at the short side of the channel near an input to a fluidic reservoir 1004, satisfying the first condition needed for an inertial pump to create a pumping effect that can generate a net fluid flow through the channel. The second condition that needs to be satisfied to create a pump effect is an asymmetric operation of the fluid actuator 1002, as noted above. The fluid actuator 1002 is generally described herein as being a piezoelectric membrane whose up and down deflections (sometimes referred to as piston strokes) within the fluidic channel generate fluid displacements that can be specifically controlled (e.g., by a controller 106). However, a variety of other devices can be used to implement the fluid actuator including, for example, a resistive heater to generate a vapor bubble, an electrostatic (MEMS) membrane, a mechanical/ impact driven membrane, a voice coil, a magneto-strictive drive, and so on.

At operating stage A shown in FIG. 10, the fluid actuator 1002 is in a resting position and is passive, so there is no net fluid flow through the channel 1000, as indicated by the legend. At operating stage B, the fluid actuator 1002 is active and the membrane is deflecting upward into the fluidic channel 1000. This upward deflection, or forward stroke, causes a compressive (positive) displacement of fluid within the channel 1000 as the membrane pushes the fluid outward. At operating stage C, the fluid actuator 1002 is active and the membrane is beginning to deflect downward to return to its original resting position. This downward deflection of the membrane, or reverse stroke, causes a tensile (negative) displacement of fluid within the channel 1000 as it pulls the fluid downward. An upward and downward deflection is one deflection cycle. A net fluid flow is generated through the channel 1000 if there is temporal asymmetry between the upward deflection (i.e., the compressive displacement) and the downward deflection in repeating deflection cycles. The question marks in FIG. 10 between opposite net flow direction arrows for the operating stages B and C merely indicate that the particular temporal asymmetry between the compressive and tensile displacements of the fluid actuator 1002 has not yet been specified, and therefore the direction of flow, if any, is not yet known. Directional flow is discussed below with reference to FIGS. 11-14.

Figure 11:
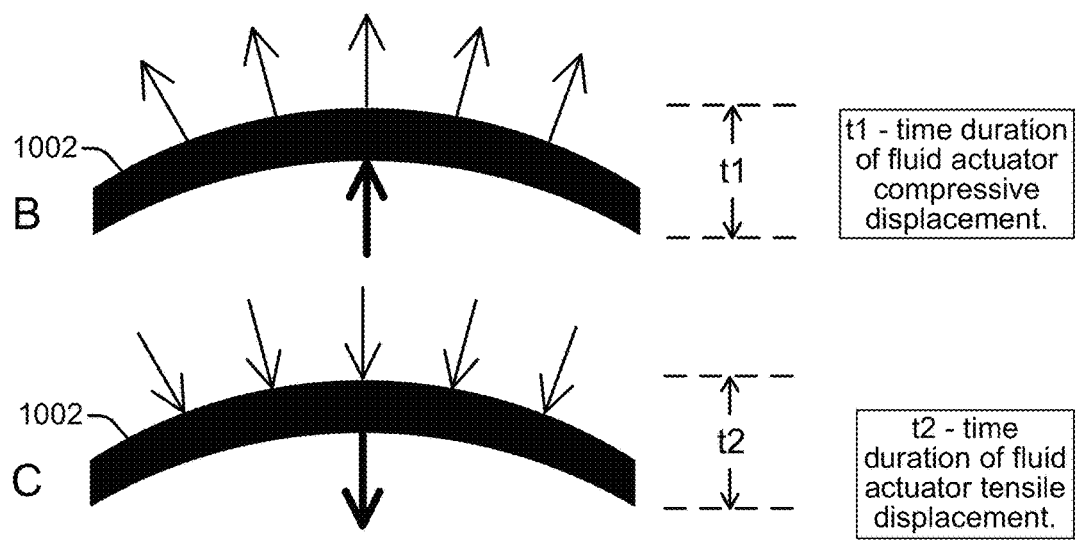
FIG. 11 shows the active fluid actuator at the operating stages from FIG. 10, according to an embodiment.

FIG. 11 shows the active fluid actuator 1002 at the operating stages B and C from FIG. 10, along with time markers "t1" and "t2" to help illustrate temporal asymmetry between compressive and tensile displacements generated by the fluid actuator 1002, according to an embodiment of the disclosure. The time t1 is the time it takes for the fluid actuator membrane to deflect upward, generating a compressive fluid displacement. The time t2 is the time it takes for the fluid actuator membrane to deflect downward, or back to its original position, generating a tensile fluid displacement. Asymmetric operation of the fluid actuator 1002 occurs if the t1 duration of the compressive displacement (upward membrane deflection) is greater or lesser than (i.e., not the same as) the t2 duration of the tensile displacement (downward membrane deflection). Such asymmetric fluid actuator operation over repeating deflection cycles generates a net fluid flow within the channel 1000. However, if the t1 and t2 compressive and tensile displacements are equal, or symmetric, there will be little or no net fluid flow through the channel 1000, regardless of the asymmetric placement of the fluid actuator 1002 within the channel 1000.

Figure 12:
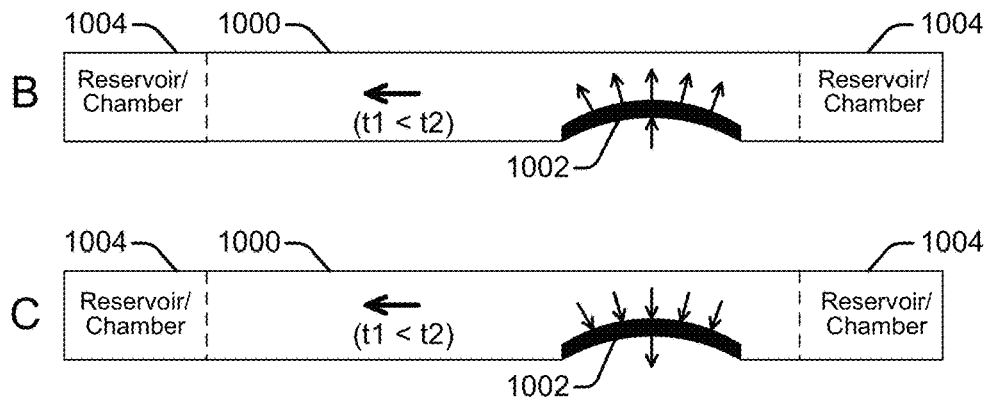
FIGS. 12, 13 and 14 show the active fluid actuator at the operating stages from FIG. 10, including net fluid flow direction arrows, according to some embodiments.
Figure 13:
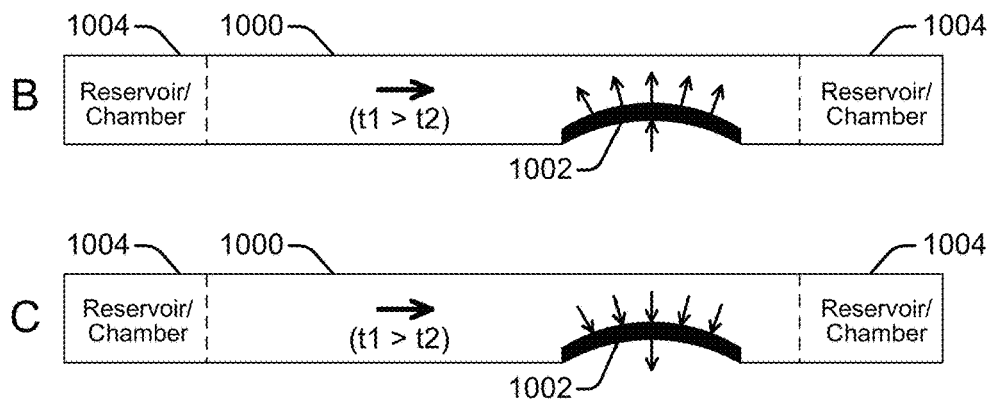
Figure 14:
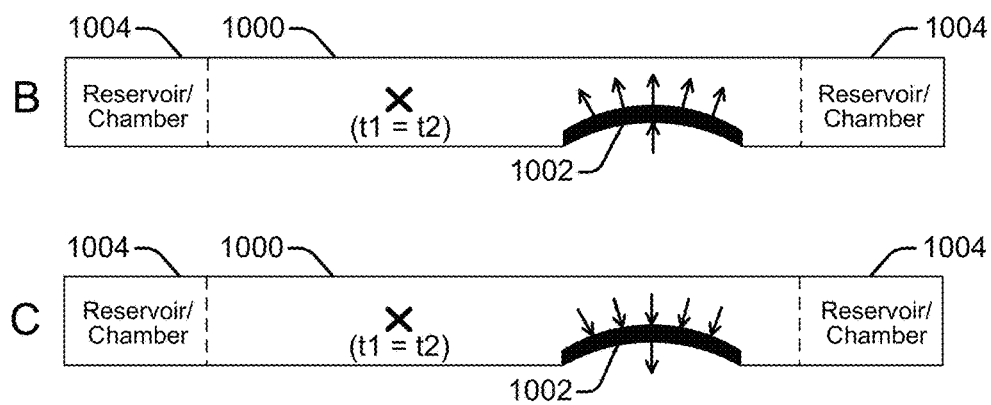
Figure 15:
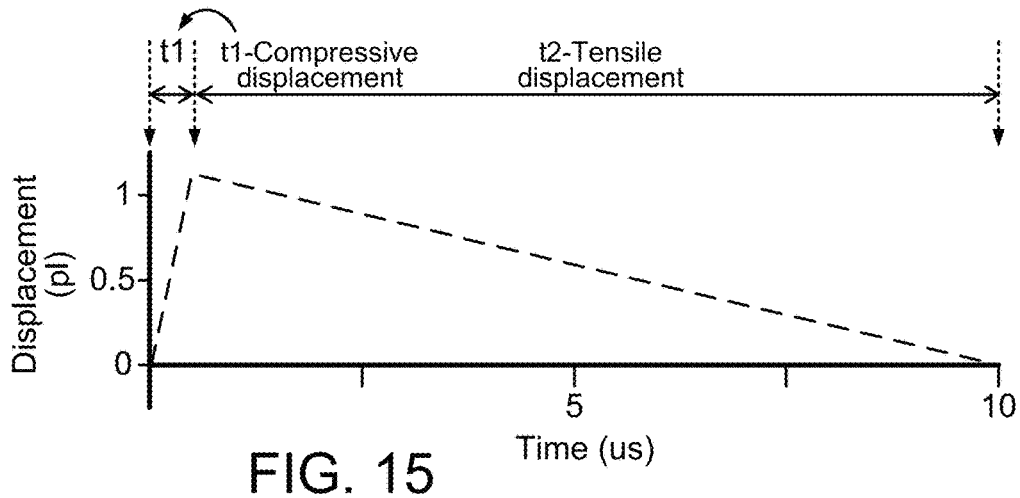
FIGS. 15, 16 and 17 show example displacement pulse waveforms, according to some embodiments.
Figure 16:
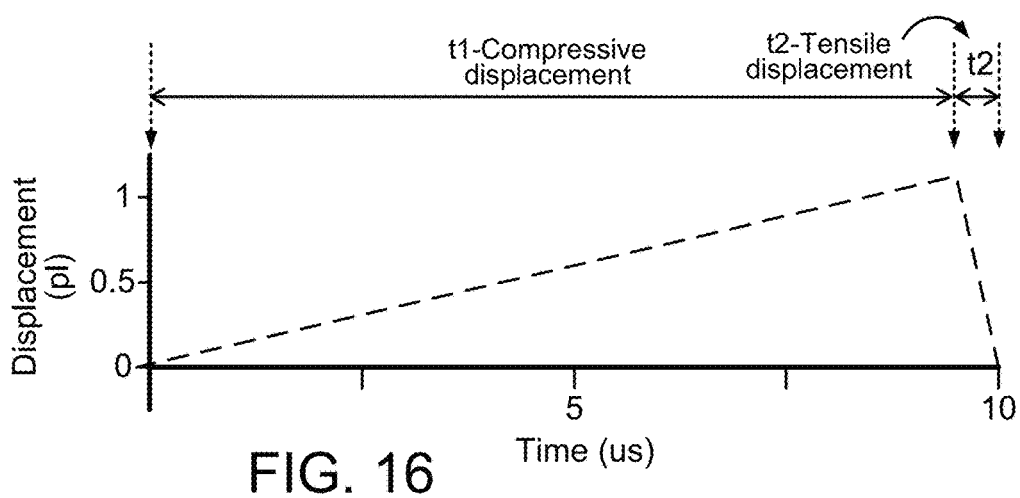
Figure 17:
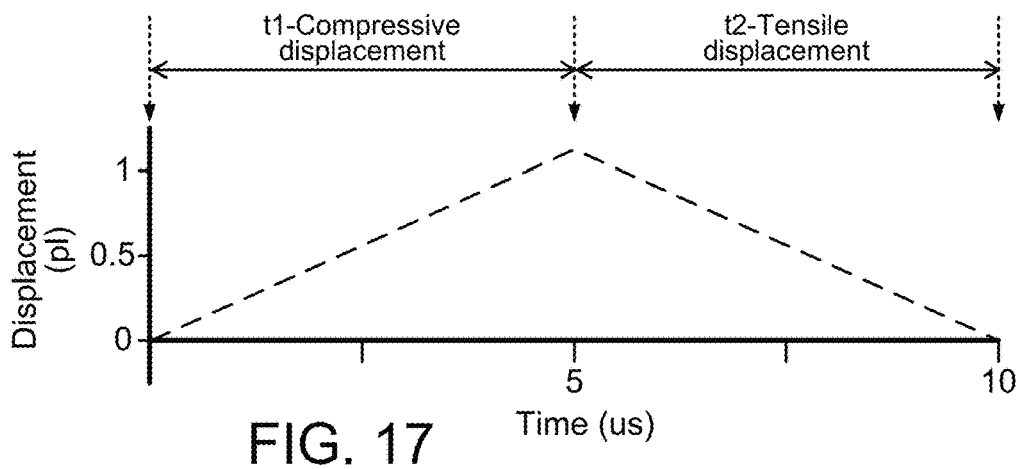

FIGS. 12, 13 and 14 show the active fluid actuator 1002 at the operating stages B and C from FIG. 10, including net fluid flow direction arrows that indicate which direction fluid flows through the channel 1000, if at all, according to embodiments of the disclosure. The direction of the net fluid flow depends on the compressive and tensile displacement durations (t1 and t2) from the actuator. FIGS. 15, 16 and 17 show example displacement pulse waveforms whose durations correspond respectively with the displacement durations t1 and t2 of FIGS. 12, 13 and 14. For various fluid pump actuators the compressive displacement and tensile displacement times, t1 and t2, can be precisely controlled by a controller 106, for example, executing instructions from an instruction module 114 (flow direction module 114) within a microfluidic system such as a polymerase chain reaction (PCR) system 100 on a PCR microchip 102.

Referring to FIG. 12, the compressive displacement duration, t1, is less than the tensile displacement duration, t2, so there is a net fluid flow in a direction from the short side of the channel 1000 (i.e., the side where the actuator is located) to the long side of the channel. The difference between the compressive and tensile displacement durations, t1 and t2, can be seen in FIG. 15 which shows a corresponding example displacement pulse waveform that might be generated by the fluid actuator with a compressive displacement duration of t1 and a tensile displacement duration of t2. The waveform of FIG. 15 indicates a displacement pulse/cycle on the order of 1 pico-liter (pl) with the compressive displacement duration, t1, of approximately 0.5 microseconds (ms) and the tensile displacement duration, t2, of approximately 9.5 ms. The values provided for the fluid displacement amount and displacement durations are only examples and not intended as limitations in any respect.

In FIG. 13, the compressive displacement duration, t1, is greater than the tensile displacement duration, t2, so there is a net fluid flow in the direction from the long side of the channel 1000 to the short side of the channel. The difference between the compressive and tensile displacement durations, t1 and t2, can be seen in FIG. 16 which shows a corresponding example displacement pulse waveform that might be generated by the fluid actuator with a compressive displacement duration of t1 and a tensile displacement duration of t2. The waveform of FIG. 16 indicates a displacement pulse/cycle on the order of 1 pico-liter (pl) with the compressive displacement duration, t1, of approximately 9.5 microseconds (ms) and the tensile displacement duration, t2, of approximately 0.5 ms.

In FIG. 14, the compressive displacement duration, t1, is equal to the tensile displacement duration, t2, so there is little or no net fluid flow through the channel 1000. The equal compressive and tensile displacement durations of t1 and t2, can be seen in FIG. 17 which shows a corresponding example displacement pulse waveform that might be generated by the fluid actuator with a compressive displacement duration of t1 and a tensile displacement duration of t2. The waveform of FIG. 17 indicates a displacement pulse/cycle on the order of 1 pico-liter (pl) with the compressive displacement duration, t1, of approximately 5.0 microseconds (ms) and the tensile displacement duration, t2, of approximately 5.0 ms.

Note that in FIG. 14, although there is asymmetric location of the fluid actuator 1002 within the channel 1000 (satisfying one condition for achieving the pump effect), there is still little or no net fluid flow through the channel 1000 because the fluid actuator operation is not asymmetric (the second condition for achieving the pump effect is not satisfied). Likewise, if the location of the fluid actuator was symmetric (i.e., located at the center of the channel), and the operation of the actuator was asymmetric, there would still be little or no net fluid flow through the channel because both of the pump effect conditions would not be satisfied.

From the above examples and discussion of FIGS. 10-17, it is useful to note the interaction between the pump effect condition of asymmetric location of the fluid actuator and the pump effect condition of asymmetric operation of the fluid actuator. That is, if the asymmetric location and the asymmetric operation of the fluid actuator work in the same direction, the fluid pump actuator will demonstrate a high efficiency pumping effect. However, if the asymmetric location and the asymmetric operation of the fluid actuator work against one another, the asymmetric operation of the fluid actuator reverses the net flow vector caused by the asymmetric location of the fluid actuator, and the net flow is from the long side of the channel to the short side of the channel 1000.

In addition, from the above examples and discussion of FIGS. 10-17, it can now be better appreciated that the fluid pump actuator 902 discussed above with respect to the inertial pump 900 of FIG. 9 (shown as a unidirectional inertial pump) is assumed to be an actuator device whose compressive displacement durations are less than its tensile displacement durations. An example of such an actuator is a resistive heating element that heats the fluid and causes displacement by an explosion of supercritical vapor. Such an event has an explosive asymmetry whose expansion phase (i.e., compressive displacement) is faster than its collapse phase (i.e., tensile displacement). The asymmetry of this event cannot be controlled in the same manner as the asymmetry of deflection caused by a piezoelectric membrane actuator, for example. However, as the examples and discussion of FIGS. 10-17 show, the fluid pump actuator 902 of FIG. 9 can also be an actuator device such as a piezoelectric membrane whose fluid displacements can be specifically controlled by controlling the durations of the up and down deflections of the membrane within the fluidic channel.

Figure 18:
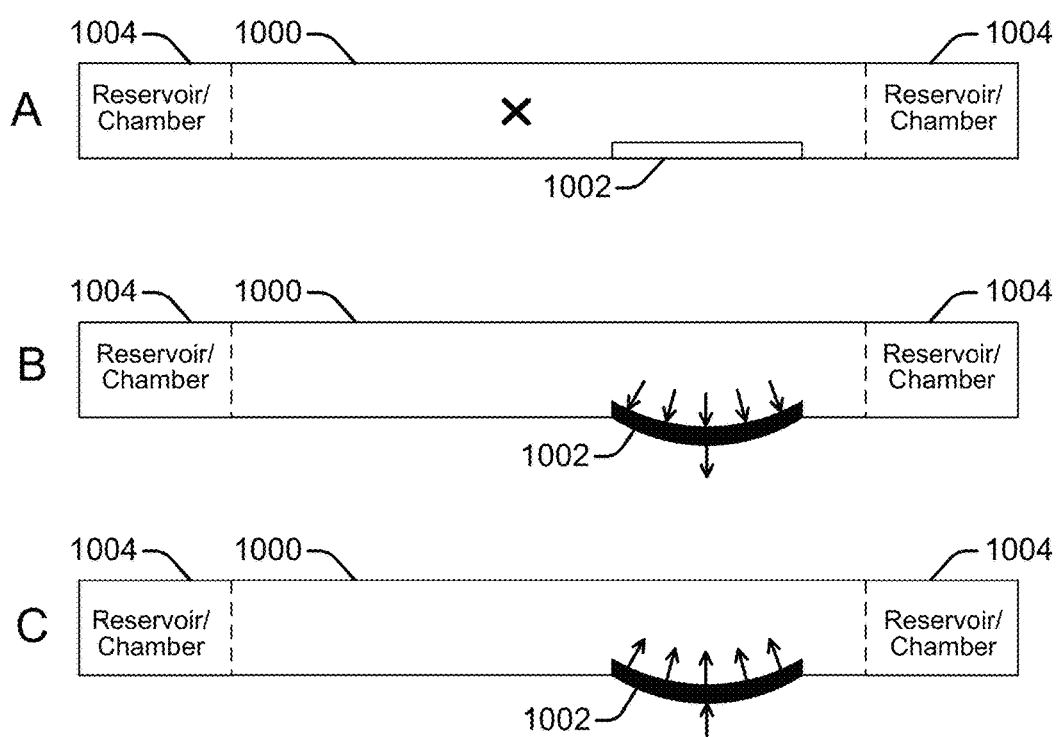
FIG. 18 shows a side view of an example microfluidic channel with an integrated inertial pump whose fluid actuator is in different stages of operation, according to an embodiment.

FIG. 18 shows a side view of an example microfluidic channel 1000 with an integrated inertial pump whose fluid actuator 1002 is in different stages of operation, according to an embodiment of the disclosure. This embodiment is similar to that shown and discussed regarding FIG. 10 above, except that the deflections of the fluid actuator membrane are shown working differently to create compressive and tensile displacements within the channel 1000. At operating stage A shown in FIG. 18, the fluid actuator 1002 is in a resting position and is passive, so there is no net fluid flow through the channel 1000. At operating stage B, the fluid actuator 1002 is active and the membrane is deflected downward and outside of the fluidic channel 1000. This downward deflection of the membrane causes a tensile displacement of fluid within the channel 1000, as it pulls the fluid downward. At operating stage C, the fluid actuator 1002 is active and the membrane is beginning to deflect upward to return to its original resting position. This upward deflection causes a compressive displacement of fluid within the channel 1000, as the membrane pushes the fluid upward into the channel. A net fluid flow is generated through the channel 1000 if there is temporal asymmetry between the compressive displacement and the tensile displacement. The direction of a net fluid flow is dependent upon the durations of the compressive and tensile displacements, in the same manner as discussed above.

Figure 19:
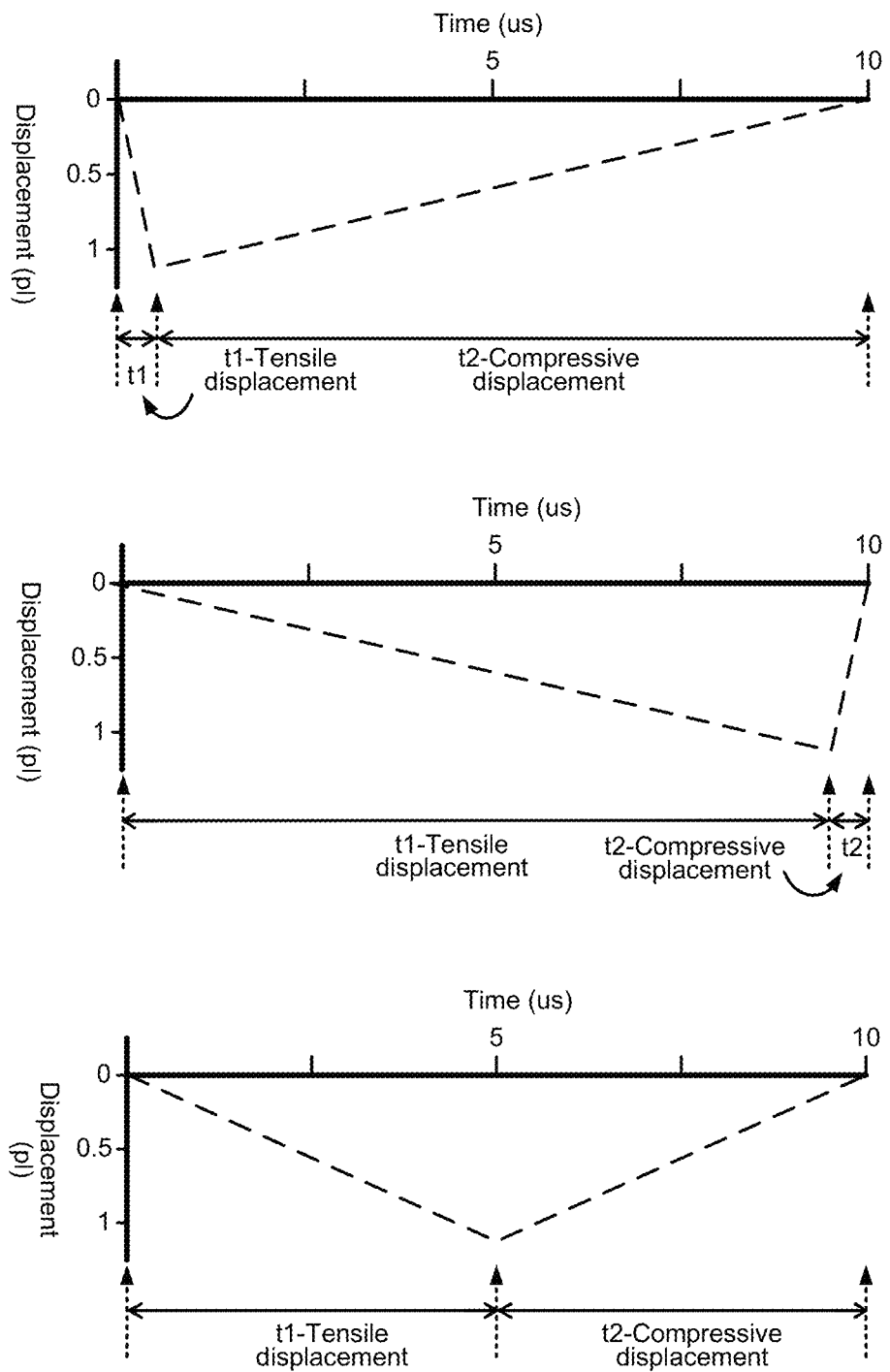
FIG. 19 shows example displacement pulse waveforms whose durations correspond with displacement durations of a fluid actuator, according to embodiments.

FIG. 19 shows example displacement pulse waveforms whose durations may correspond respectively with displacement durations t1 and t2 of the actuator 1002 of FIG. 18, according to embodiments of the disclosure. The waveforms in FIG. 19 show the tensile (negative) displacement occurring before the compressive (positive) displacement. In both the previous examples discussed above, the fluid actuator 1002 begins in a resting position and then either produces a compressive (positive) displacement followed by a tensile (negative) displacement, or it produces a tensile displacement followed by a compressive displacement. However, various other displacement examples and corresponding waveforms are possible. For example, the fluid actuator 1002 can be pre-loaded in a particular direction and/or it can traverse its resting position such that it deflects both into the channel 1000 and out of the channel 1000 as it produces compressive and tensile displacements.

Figure 20:
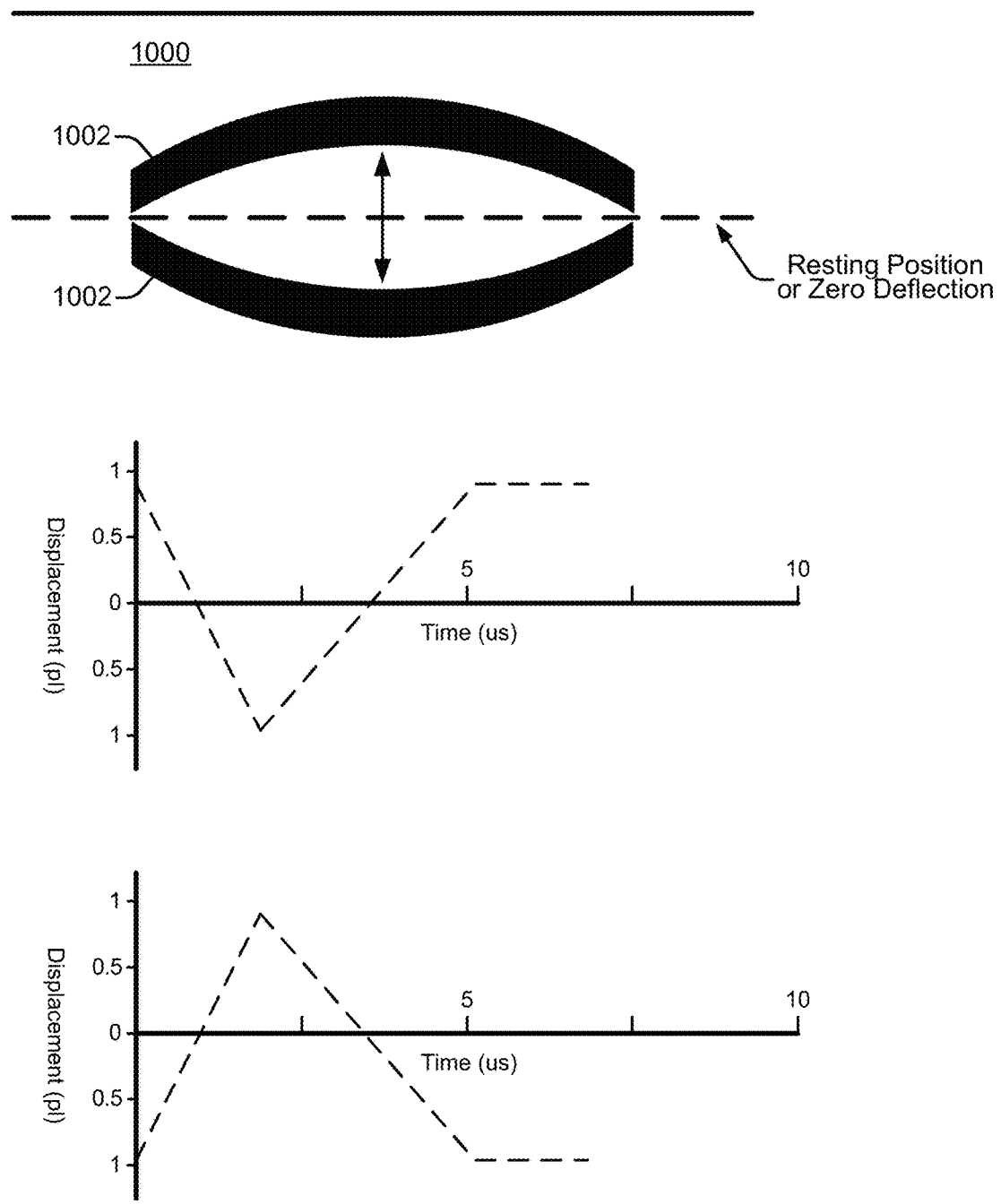
FIG. 20 shows an example representation of a fluid actuator deflecting both into and out of a channel, along with representative displacement pulse waveforms, according to an embodiment.

FIG. 20 shows an example representation of a fluid actuator 1002 deflecting both into and out of a microfluidic channel 1000, along with representative displacement pulse waveforms to illustrate both how the actuator 1002 can deflect into the channel 1000 and out of the channel 1000 as it produces compressive and tensile displacements and the possible pre-loading of the actuator 1002 in a positive or negative deflection. Such deflections of the actuator 1002 into and out of channel 1000 and pre-loading of the actuator 1002 are controlled, for example, by instruction modules (e.g., flow direction module 114, flow rate module 116) executing on electronic controller 106.

What is claimed is:

1. A polymerase chain reaction (PCR) system comprising:
a first chamber and a second chamber fluidically coupled to one another through a microfluidic channel;
an inertial pump associated with the microfluidic channel associated and including a fluid actuator integrated asymmetrically within the microfluidic channel; and
a controller configured to cause circulation of a fluidic PCR mixture from the first chamber to the second chamber by repeatedly actuating the fluid actuator over a plurality of deflection cycles between a non-deflected state in which the fluid actuator is not deflected into the microfluidic channel and a deflected state in which the fluid actuator is deflected into the microfluidic channel, wherein circulation of the fluidic PCR mixture does not occur and the fluid actuator remains at rest in the non-deflected state when the controller is not actuating the fluid actuator.

2. The PCR system of claim 1, wherein the fluid actuator is thermally driven and electronically controlled.

3. The PCR system of claim 1, wherein the inertial pump comprises a bidirectional inertial pump and the fluid actuator is controllable to generate compressive and tensile fluid displacements of varying durations.

4. The PCR system of claim 1, wherein the inertial pump is selected from a group consisting of bidirectional pumps and unidirectional pumps.

5. The PCR system of claim 1, wherein actuating the fluid actuators comprise controlling compressive and tensile fluid displacement durations of the fluid actuator.

6. The PCR system of claim 1, further comprising a microchip on which the chamber, the microfluidic channel and the inertial pump are fabricated.

7. The PCR system of claim 1, wherein first and the second chambers comprise:
temperature sensors to sense the temperatures of the first and the second chambers; and
resistive heaters to maintain the temperatures in the first and the second chambers within controlled temperature ranges according to sensed temperatures from the temperature sensors.

8. The PCR system of claim 7, further comprising:
a temperature control module executable on the controller to monitor the temperature sensors and activate the resistive heaters such that each of the first and the second chambers is maintained within a controlled temperature range.

9. The PCR system of claim 1, wherein the first and the second chambers each comprise one of a linear PCR architecture with a denature chamber, an annealing chamber, an extension chamber, and a product chamber.

10. The PCR system of claim 9, comprising a plurality of the linear PCR architectures on a microchip capable of parallel PCR processing.

11. The PCR system of claim 1, wherein the first and the second chambers each comprise one of a denature chamber, a mixture chamber, an annealing chamber, and an extension chamber.

12. The PCR system of claim 11, comprising a plurality of the circular PCR architectures on a microchip capable of parallel PCR processing.

13. A polymerase chain reaction (PCR) method comprising:
repeatedly actuating, over a plurality of deflection cycles, a fluid actuator integrated asymmetrically within a microfluidic channel associated with an inertial pump;
circulating a fluidic PCR mixture from a first chamber and a second chamber fluidically coupled to one another through the microfluidic channel, via the repeated actuation of the fluid actuator over the deflection cycles transitioning the fluid actuator between a non-deflected state in which the fluid actuator is not deflected into the microfluidic channel and a deflected state in which the fluid actuator is deflected into the microfluidic channel,
wherein circulation of the fluidic PCR mixture does not occur and the fluid actuator remains at rest in the non-deflected state when the fluid actuator is not being actuated.

14. The PCR method of claim 13, further comprising thermally driving and electronically controlling the fluid actuator.

15. The PCR method of claim 13, further comprising generating compressive and tensile fluid displacements of varying directions via control of the fluid actuator, the inertial pump being a bidirectional inertial pump.

16. The PCR method of claim 13, further controlling activation of the fluid actuator by controlling compressive and tensile fluid displacement durations of the fluid actuator.

17. The PCR method of claim 13, further comprising:
monitoring temperatures of the chambers;
activating resistive heaters associated with the first and second chambers to maintain the temperatures of the first and second chambers within a controlled temperature range.

18. A method comprising:
providing a first chamber and a second chamber;
providing a microfluidic channel fluidically coupling the first and second chambers;
providing an inertial pump associated with a microfluidic channel and including a fluid actuator integrated asymmetrically within the microfluidic channel; and
providing a controller configured to cause circulation of a fluidic PCR mixture from the first chamber to the second chamber by repeatedly actuating the fluid actuator over a plurality of deflection cycles between a non-deflected state in which the fluid actuator is not deflected into the microfluidic channel and a deflected state in which the fluid actuator is deflected into the microfluidic channel,
wherein circulation of the fluidic PCR mixture does not occur and the fluid actuator remains at rest in the non-deflected state when the controller is not actuating the fluid actuator.

19. The method of claim 18, wherein the first and second chambers, the microfluidic channel, and the inertial pump are fabricated on a microchip.

* * * * *